United States Patent [19]

Sadler et al.

[11] Patent Number: 5,028,534

[45] Date of Patent: Jul. 2, 1991

[54] DNA CLONES OF HUMAN PLACENTAL PLASMINOGEN ACTIVATOR INHIBITOR

[75] Inventors: J. Evan Sadler; Tze-Chein Wun, both of St. Louis, Mo.

[73] Assignees: Washington Univ.; Monsanto Company, both of St. Louis, Mo.

[21] Appl. No.: 97,482

[22] Filed: Sep. 15, 1987

[51] Int. Cl.$^5$ ................... C12N 15/15; C12N 15/03; C12N 15/06; C12P 21/02

[52] U.S. Cl. ................... 435/69.2; 435/69.1; 435/240.1; 435/240.2; 435/252.3; 435/320.1; 536/27; 935/11; 935/29; 935/32; 935/70; 935/73

[58] Field of Search ............ 435/69.1, 69.2, 172.1, 435/172.3, 320, 252.3, 252.35, 240.2, 68, 70; 536/27; 935/11, 29, 32, 70, 73; 527/27

[56] References Cited

U.S. PATENT DOCUMENTS 4,551,433  11/1985  DeBoer .................. 435/68 X

OTHER PUBLICATIONS

Casson, J. et al, *Nature*, vol. 315, pp. 768–771, 1985.
Sadler, J. et al, *Proc. Natl. Acad. Sci.*, vol. 82, pp. 6394–6398, 1985.
Schleuning, W. et al, *Molec & Cell Biol.*, vol. 7, pp. 4564–4567, Dec. 1987.
Webb, A. et al, *J. Exp Med.*, vol. 166, pp. 77–94, Jul. 1987.
Kawano et al., Nature 217, 253–254 (1968).
Astedt et al., Thromb. Haemostas. 53, 122–125 (1985).
Wun and Reich, J. Biol. Chem. 262, 3646–3653 (1987).
Chapman et al., Cell 28, 653–662 (1982).
Kopitar et al., Thromb. Haemostasis, 54, 750–755 (1985).
Vassalli et al., J. Exp. Med. 159, 1653–1668 (1984).
Kruithof et al., J. Biol. Chem. 261, 11207–11213 (1986).
Sprengens and Kluft, Blood 69, 381–387 (1987).
Ye et al, J. Biol. Chem. 262, 3718–3725 (1987).

*Primary Examiner*—James Martinell
*Attorney, Agent, or Firm*—Scott J. Meyer; James W. Williams, Jr.

[57] ABSTRACT cDNA clones having a base sequence for human placental plasminogen activator inhibitor (PAI-2) have been developed and characterized and the amino acid sequence of the PAI-2 has been determined. The PAI-2 protein has then been expressed in prokaryotic and eukaryotic cells.

8 Claims, 6 Drawing Sheets

```
-55  GTTAC CCGTCAGACA GCAACTCAGA GAATAACCAG AGAACAACCA GATTGAAACA    -1

ATG GAG GAT CTT TGT GTG GCA AAC ACA CTC TTT GCC CTC AAT TTA
     Met Glu Asp Leu Cys Val Ala Asn Thr Leu Phe Ala Leu Asn Leu
                                10
     TTC AAG CAT CTG GCA AAA GCA AGC CCC ACC CAG AAC CTC TTC CTC     90
     Phe Lys His Leu Ala Lys Ala Ser Pro Thr Gln Asn Leu Phe Leu
                 20                                      30
     TCC CCA TGG AGC ATC TCG TCC ACC ATG GCC ATG GTC TAC ATG GGC
     Ser Pro Trp Ser Ile Ser Ser Thr Met Ala Met Val Tyr Met Gly
                                40
     TCC AGG GGC AGC ACC GAA GAC CAG ATG GCC AAG GTG CTT CAG TTT    180
     Ser Arg Gly Ser Thr Glu Asp Gln Met Ala Lys Val Leu Gln Phe
                 50                                      60
     AAT GAA GTG GGA GCC AAT GCA GTT ACC CCC ATG ACT CCA GAG AAC
     Asn Glu Val Gly Ala Asn Ala Val Thr Pro Met Thr Pro Glu Asn
                                70                       *
     TTT ACC AGC TGT GGG TTC ATG CAG CAG ATC CAG AAG GGT AGT TAT    270
     Phe Thr Ser Cys Gly Phe Met Gln Gln Ile Gln Lys Gly Ser Tyr
                 80                                      90
     CCT GAT GCG ATT TTG CAG GCA CAA GCT GCA GAT AAA ATC CAT TCA
     Pro Asp Ala Ile Leu Gln Ala Gln Ala Ala Asp Lys Ile His Ser
                                100
     TCC TTC CGC TCT CTC AGC TCT GCA ATC AAT GCA TCC ACA GGG GAT    360
     Ser Phe Arg Ser Leu Ser Ser Ala Ile Asn Ala Ser Thr Gly Asp
                 110                 *                   120
     TAT TTA CTG GAA AGT GTC AAT AAG CTG TTT GGT GAG AAG TCT GCG
     Tyr Leu Leu Glu Ser Val Asn Lys Leu Phe Gly Glu Lys Ser Ala
                                130
     AGC TTC CGG GAA GAA TAT ATT CGA CTC TGT CAG AAA TAT TAC TCC    450
     Ser Phe Arg Glu Glu Tyr Ile Arg Leu Cys Gln Lys Tyr Tyr Ser
                 140                                     150
```

FIG. 4A

```
TCA GAA CCC CAG GCA GTA GAC TTC CTA GAA TGT GCA GAA GAA GCT
Ser Glu Pro Gln Ala Val Asp Phe Leu Glu Cys Ala Glu Glu Ala
                                    160
AGA AAA AAG ATT AAT TCC TGG GTC AAG ACT CAA ACC AAA GGC AAA      540
Arg Lys Lys Ile Asn Ser Trp Val Lys Thr Gln Thr Lys Gly Lys
                170                                     180

ATC CCA AAC TTG TTA CCT GAA GGT TCT GTA GAT GGG GAT ACC AGG
Ile Pro Asn Leu Leu Pro Glu Gly Ser Val Asp Gly Asp Thr Arg
                                        190
ATG GTC CTG GTG AAT GCT GTC TAC TTC AAA GGA AAG TGG AAA ACT      630
Met Val Leu Val Asn Ala Val Tyr Phe Lys Gly Lys Trp Lys Thr
                200                                     210

CCA TTT GAG AAG AAA CTA AAT GGG CTT TAT CCT TTC CGT GTA AAC
Pro Phe Glu Lys Lys Leu Asn Gly Leu Tyr Pro Phe Arg Val Asn
                                    220
TCG GCT CAG CGC ACA CCT GTA CAG ATG ATG TAC TTG CGT GAA AAG      720
Ser Ala Gln Arg Thr Pro Val Gln Met Met Tyr Leu Arg Glu Lys
                230                                     240

CTA AAC ATT GGA TAC ATA GAA GAC CTA AAG GCT CAG ATT CTA GAA
Leu Asn Ile Gly Tyr Ile Glu Asp Leu Lys Ala Gln Ile Leu Glu
                                        250
CTC CCA TAT GCT GGA GAT GTT AGC ATG TTC TTG TTG CTT CCA GAT      810
Leu Pro Tyr Ala Gly Asp Val Ser Met Phe Leu Leu Leu Pro Asp
                260                                     270

GAA ATT GCC GAT GTG TCC ACT GGC TTG GAG CTG CTG GAA AGT GAA
Glu Ile Ala Asp Val Ser Thr Gly Leu Glu Leu Leu Glu Ser Glu
                                        280
ATA ACC TAT GAC AAA CTC AAC AAG TGG ACC AGC AAA GAC AAA ATG      900
Ile Thr Tyr Asp Lys Leu Asn Lys Trp Thr Ser Lys Asp Lys Met
                290                                     300

GCT GAA GAT GAA GTT GAG GTA TAC ATA CCC CAG TTC AAA TTA GAA
Ala Glu Asp Glu Val Glu Val Tyr Ile Pro Gln Phe Lys Leu Glu
                310
GAG CAT TAT GAA CTC AGA TCC ATT CTG AGA AGC ATG GGC ATG GAG      990
Glu his Tyr Glu Leu Arg Ser Ile Leu Arg Ser Met Gly Met Glu
                320                                     330
```

FIG. 4B

```
GAC GCC TTC AAC AAG GGA CGG GCC AAT TTC TCA GGG ATG TCG GAG
Asp Ala Phe Asn Lys Gly Arg Ala Asn Phe Ser Gly Met Ser Glu
                            *  340
AGG AAT GAC CTG TTT CTT TCT GAA GTG TTC CAC CAA GCC ATG GTG    1080
Arg Asn Asp Leu Phe Leu Ser Glu Val Phe His Gln Ala Met Val
                350                                 360

GAT GTG AAT GAG GAG GGC ACT GAA GCA GCC GCT GGC ACA GGA GGT
Asp Val Asn Glu Glu Gly Thr Glu Ala Ala Ala Gly Thr Gly Gly
                                    370
GTT ATG ACA GGG AGA ACT GGA CAT GGA GGC CCA CAG TTT GTG GCA    1170
Val Met Thr Gly Arg Thr Gly His Gly Gly Pro Gln Phe Val Ala
                380                                 390

GAT CAT CCG TTT CTT TTT CTT ATT ATG CAT AAG ATA ACC AAG TGC
Asp His Pro Phe Leu Phe Leu Ile Met His Lys Ile Thr Lys Cys
                                    400
ATT TTA TTT TTC GGC AGA TTT TGC TCA CCC TAA AAC TAA GCG TGC    1260
Ile Leu Phe Phe Gly Arg Phe Cys Ser Pro End
                410
```

TGCTTCTGCA AAAGATTTTT GTAGATGAGC TGTGTGCCTC AGAATTGCTA TTTCAAATTG
CCAAAAATTT AGAGATGTTT TCTACATATT TCTGCTCTTC TGAACAACTT         1370
CTGCTACCCA CTAAATAAAA ACACAGAAAT AATTAGACAA TTGTCTATTA TAACATGACA
ACCCTATTAA TCATTTGGTC TTCTAAAATG GGATCATGCC CATTTAGATT         1480
TTCCTTACTA TCAGTTTATT TTTATAACAT TAACTTTTAC TTTGTTATTT ATTATTTTAT
ATAATGGTGA GTTTTTAAAT TATTGCTCAC TGCCTATTTA ATGTAGCTAA         1590
TAAAGTTATA GAAGCAGATG ATCTGTTAAT TTCCTATCTA ATAAATGCCT TTAATTGTTC
TCATAATGAA GAATAAGTAG GTATCCCTCC ATGCCCTTCT ATAATAAATA         1700
TCTGGAAAAA ACATTAAACA ATAGGCAAAT ATATGTTATG TGCATTTCTA GAAATACATA
ACACATATAT ATGTCTGTAT CTTATATTCA ATTGCAAGTA TATAATAAAT         1810
AAACCTGCTT CCAAACAACA AAAAAAAAAA AAAAAAAAAA AAAAA             1855

FIG. 4C

DNA CLONES OF HUMAN PLACENTAL PLASMINOGEN ACTIVATOR INHIBITOR

BACKGROUND OF THE INVENTION

This invention relates to a plasminogen activator inhibitor and, more particularly, to cDNA clones representing essentially a full size plasminogen activator inhibitor of the placental type and to expression of the recombinant protein in prokaryotic and eukaryotic hosts.

The plasminogen activators are a class of serine proteases that convert plasminogen to the fibrinolytically active enzyme plasmin (fibrinolysin). Upon being thus activated, the plasmin can attack the coagulation proteins of the fibrin clot (thrombus) and thereby disintegrate the clot. Inhibitors normally present in the blood with plasminogen generally retard this reaction.

Human plasma contains two plasminogen activators that are immunologically distinct, namely tissue plasminogen activator (t-PA) and urokinase (u-PA). t-PA has been demonstrated to have higher affinity for fibrin than u-PA and, therefore, is a preferable agent for degradation of the fibrin clot. The source of the plasma t-PA has been presumed to be the vascular endothelium.

Plasminogen activator inhibitors (PAI) have been obtained from various sources. They are now classified in at least three immunologically different groups: protease nexin-I, the endothelial cell type plasminogen activator inhibitor (PAI-1), and the placental type plasminogen activator inhibitor (PAI-2).

Protease nexin-I was isolated from human fibroblasts and has an apparent $M_r$ 43 kilodaltons (kDa). Scott et al., *J. Biol. Chem.* 260 (11), 7029–7034 (1985). It is distinguished by its acid lability, its ability to inhibit both plasminogen activators and plasmin, its relatively high pI (7.5–7.8) and by the stimulatory effect of heparin on its activity.

Endothelial cell-type PAI-1 is a glycoprotein of $M_r$ 50–54 kDa that rapidly inactivates both t-PA and μ-PA. It is synthesized by endothelial cells and certain hepatoma and fibrosarcoma lines. It is found in platelets and is believed to constitute the major PAI of normal human plasma. See Pannekoek et al., *The EMBO Journal* 5 (10), 2539–2544 (1986); Andreason et al., *FEBS Lett.* 209 (2), 213–218 (1986); Ginsburg et al., *J. Clin. Invest.* 98, 1673–1680 (1986); and Wun and Kretzmer, *FEBS Lett.* 210, 11–16 (1987).

Placenta-type PAI-2 is a distinct protein of $M_r$ 47,000. Kawano et al., *Nature* 217, 253–254 (1968); Astedt et al., *Thromb. Haemostasis* 53, 122–125 (1985); and Wun and Reich, *J. Biol. Chem.* 262, 3646–3653 (1987). It appears to be immunologically and biochemically identical to a similar activity of human monocytes Chapman et al., *Cell* 28, 653–662 (1982), and Kopitar et al., *Thromb. Haemostasis* 54, 750–755 (1985)], and monocytic cell lines [Vassalli et al., *J. Exp. Med.* 159, 1653–1668 (1984), and Kruithof et al., *J. Biol. Chem.* 261, 11207–11213 (1986)].

Further background information on the plasminogen activator inhibitors can be had by reference to the recent review article by Sprengers and Kluft, *Blood* 69(2), 381–387 (1987).

Recent advances in biochemistry and in recombinant DNA technology have made it possible to synthesize specific proteins, for example, enzymes, under controlled conditions independent of the organism from which they are normally isolated. These biochemical synthetic methods employ enzymes and subcellular components of the protein synthesizing systems of living cells, either in vitro in cell-free systems, or in vivo in microorganisms. In either case, the principal element is provision of a deoxyribonucleic acid (DNA) of specific sequence which contains the information required to specify the desired amino acid sequence. Such a specific DNA sequence is termed a gene. The coding relationships whereby a deoxyribonucleotide sequence is used to specify the amino acid sequence of a protein is well-known and operates according to a fundamental set of principles. See, for example, Watson, *Molecular Biology of the Gene*, 3d ed., Benjamin-Cummings, Menlo Park, Calif., 1976.

A cloned gene may be used to specify the amino acid sequence of proteins synthesized by in vitro systems. RNA-directed protein synthesizing systems are well-established in the art. Double-stranded DNA can be induced to generate messenger RNA (mRNA) in vitro with subsequent high fidelity translation of the RNA sequence into protein.

It is now possible to isolate specific genes or portions thereof from higher organisms, such as man and animals, and to transfer the genes or fragments to microorganisms such as bacteria (e.g., *E. coli*) or yeasts (e.g., *S. cerevisiae*). The transferred gene is replicated and propagated as the transformed microorganism replicates. Consequently, the transformed microorganism is endowed with the capacity to make the desired protein or gene which it encodes, for example, an enzyme, and then passes on this capability to its progeny. See, for example, Cohen and Boyer, U.S. Pat. Nos. 4,237,224 and 4,468,464. Likewise, mammalian cells (e.g., mouse, bovine, and Chinese hamster ovary) can be used for the expression of mammalian protein by conventional recombinant DNA methods. See, for example, Axel et al., *Science* 209, 1414–1424 (1980) and U.S. Pat. No. 4,399,216.

To illustrate, a bacterial plasmid, for example, pSC101 or pBR322 and derivatives thereof, can be used as a cloning vehicle to introduce a foreign or exogenous gene into the host bacteria. An illustrative host bacteria can be, for example, *Escherichia coli* K-12$_x$1776, which is available from the American Type Culture Collection, Rockville, Md. under accession number ATCC 31244. The plasmid can be cleaved with a restriction endonuclease or other DNA cleaving enzyme, for example EcoR I, to form a linear DNA fragment having an intact replicon and cohesive termini. A second DNA fragment having the desired exogenous or foreign gene and a given phenotypical property and complementary ligatable termini can be obtained from a foreign cell or chemically synthesized. This second DNA fragment is spliced with the first DNA fragment with a DNA ligase or other DNA ligating agent, for example T$_4$DNA Ligase, to form a completely closed and recircularized plasmid. The insertion of the second DNA fragment into the EcoR I site of the illustrative plasmid brings the expression of the genetic information under the control elements of the plasmid. The resulting recombinant plasmid is then used for transformation of the bacterial cell and allowed to replicate by growing the bacteria in a suitable culture medium. The desired transformants are then isolated by phenotypical trait differentiation, for example, by resistance to particular growth-inhibit-

BRIEF DESCRIPTION OF THE INVENTION

In accordance with the present invention, the complete coding sequence of cDNA clones representing essentially a full size plasminogen activator inhibitor of the placental type (PAI-2) has been developed. Active recombinant PAI-2 protein was expressed in prokaryotic and eukaryotic hosts by operably inserting the PAI-2 coding sequence in replicable expression vectors.

Initially, two nearly full-length cDNAs for the PAI-2 were isolated from a human placenta λgt11 cDNA library. One positive, λPAI-75.1, expressed a protein that could adsorb and purify anti-PAI antibodies. The expressed protein inhibited the activity of human urokinase in a fibrin autography assay, and formed a 79-kDa (reduced) covalent complex with $^{125}I$-urokinase that could be immunoprecipitated with anti-PAI. The largest clone, λPAI-75.15, contains a 1909 base pair (bp) cDNA insert with a 5'-noncoding region of 55 bp, an open reading frame of 1245 bp, a stop codon, a 3'-noncoding region of 581 bp, and a poly(A) tail of 25 bp.

The cDNA sequence encodes a 46.6 kDa protein of 415 amino acids. The translated protein sequence is related to members of the serpin gene family, particularly ovalbumin and the chicken gene Y protein. Like these avian proteins, the PAI-2 appears to lack a cleavable $NH_2$-terminal signal peptide. Residues 347–376 of the PAI-2 exactly match the 30 residues of the sequence reported for a PAI purified from the human monocytic cell line U-937 by Kruithof et al., supra.

There are three potential glycosylation sites in the PAI-2 protein with the sequence Asn-X-Ser/Thr, wherein X can be any of the common 20 amino acids. These sites are at amino acid positions Asn 75, Asn 115, and Asn 339.

The original source of the protein material for developing the PAI-2 cDNA was human placental tissue. Such tissue is widely available after delivery by conventional surgical procedures. cDNA libraries in the expression vector λgt11, were constructed from human placenta RNA and screened for positive clones. The λgt11 (lac5 nin5 c1857 S100) used herein is a well-known and commonly available lambda phage expression vector. It's construction and restriction endonuclease map is described by Young and Davis, *Proc. Natl. Acad. Sci. USA* 80, 1194–1198 (1983).

The active recombinant PAI-2 protein was expressed in *E. coli* cells to illustrate a prokaryotic host and in mouse C-127 cells to illustrate a eukaryotic host. The PAI-2 coding sequence illustrated by λPAI-75.1 was inserted into conventional expression vectors (plasmids) illustrated by the trp-lac promoter vector, pKK 223-3, for production in *E. coli* and the bovine papilloma virus (BPV) vector for production in mouse cells. Many clones of these recombinant cells expressed relatively high levels of the PAI-2. The PAI-2 protein expressed in mouse cells is believed to be glycosylated whereas the corresponding protein produced in *E. coli* is believed to be non-glycosylated. This is in accordance with the understanding that proteins anchored on, or secreted by eukaryotic cells are generally glycosylated whereas most prokaryotic cells do not produce glycoproteins. In both cases, the PAI-2 protein was essentially free of other proteins or peptides of human origin.

DETAILED DESCRIPTION OF THE INVENTION

Figure 1:
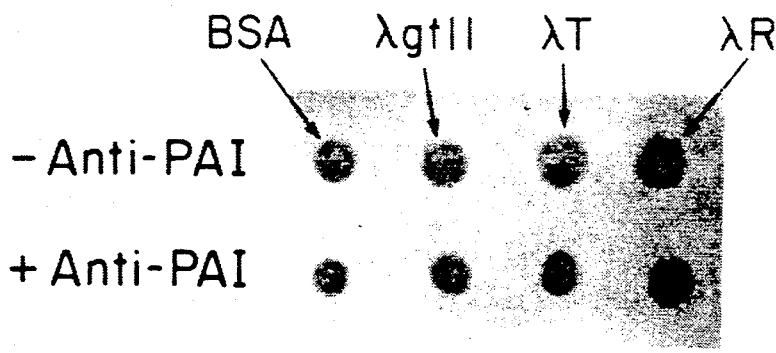

While the specification concludes with claims particularly pointing out and distinctly claiming the subject matter regarded as forming the present invention, it is believed that the invention will be better understood from the following detailed description of preferred embodiments of the invention in conjunction with the appended drawings, in which briefly:

FIG. 1 shows urokinase inhibitory activities in λgt11 fusion proteins in a fibrin-agar spot assay. Phage lysates were preincubated with anti-PAI antibody (+anti-PAI) or with preimmune serum (-anti-PAI) and then tested for PAI activity. Urokinase activity is indicated by the appearance of a clear lytic zone, and PAI activity is shown by abolishment of the lytic zone. Lysates tested were from λPAI-75.1 (λ75.1), λPAT-75.2 (λ75.2), λPAI-T (λT), λPAI-R (λR), λPAI-89.2 (λ89.2), λPAI-89.3 (λ89.3), λgt11 without insert (λgt11), and a bovine serum albumin control (BSA).

Figure 2:
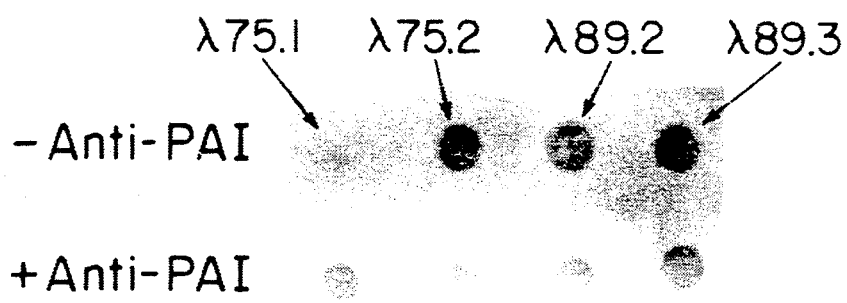

FIG. 2 shows the SDS-PAGE analysis of the complex formation between $^{125}I$-urokinase and the PA inhibitors in the phage lysates. Phage lysates containing fusion proteins from six positive clones were incubated with $^{125}I$-urokinase, immunoprecipitated by anti-placenta PAI antibodies, and electrophoresed on a 7.5% polyacrylamide gel, as described hereinafter. Gel lanes were as follows: lane 1, PBB solution; lane 2, λgt11 lysate; lane 3, λPAI-T lysate; lane 4, λPAI-R lysate; lane 5, λPAI-75.1 lysate, lane 6, λPAI-75.2 lysate; lane 7, λPAI-89.2 lysate; lane 8, λPAI-89.3 lysate. Molecular weights of complexes are indicated at the left. The band at the bottom of lane 5 represents the light chain of urokinase ($M_r$ 20,000).

Figure 3:
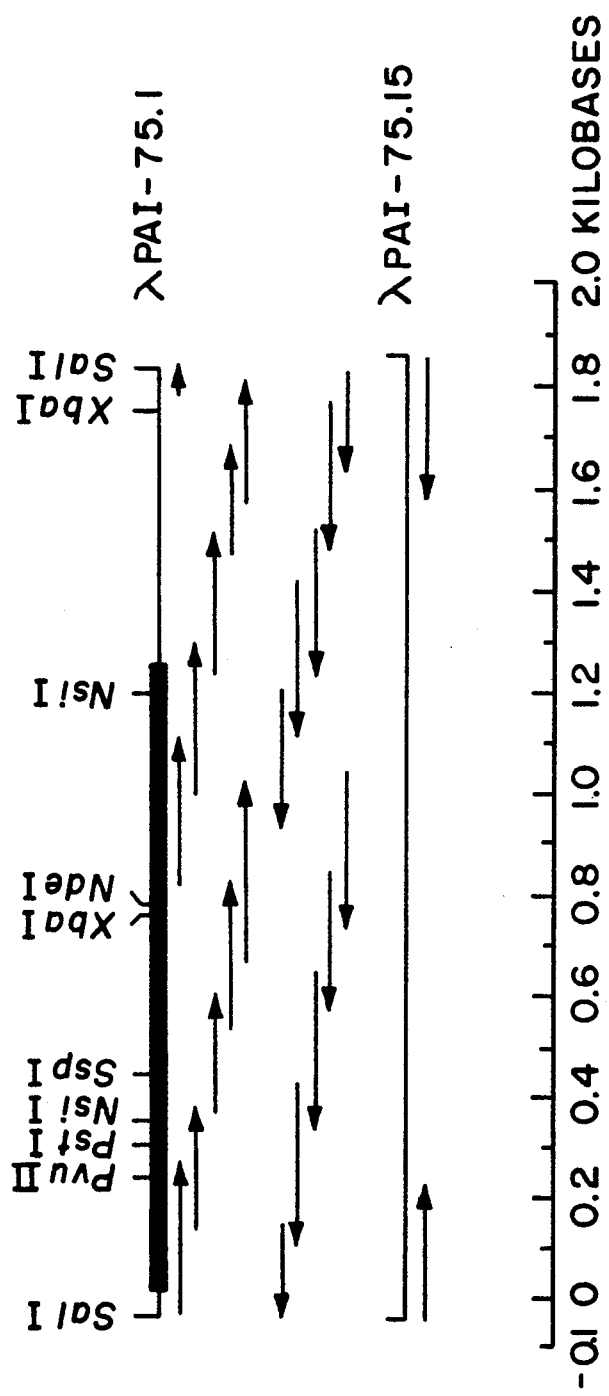

FIG. 3 shows a partial restriction map and sequencing strategy for the λPAI-75.1 and λPAI-75.15 inserts. The scale at the bottom indicates the nucleotide positions relative to the protein initiation codon. The thick bar represents the coding region for the 415 amino acids of the placental PAI. The restriction endonuclease sites shown were confirmed by digestion.

FIG. 4 shows the nucleotide sequence and translated amino acid sequences of the human placenta PAI cDNA. Nucleotides are numbered on the right-hand side. Nucleotide 1 was assigned to the A of the ATG that encodes the first methionine. Negative numbers refer to the 5'-noncoding region. Amino acids are numbered underneath the sequence. Potential N-linked glycosylation sites are marked by asterisks. The proposed reactive center is indicated by arrowheads. Potential polyadenylation signals are underlined. Sequence from nucleotides −52 to 1829 was derived from λPAI-75.1 and was determined on both strands of the cDNA. The first three nucleotides (GTT) and the poly(A) tail were determined on one strand from the λPAI-75.15 insert. The 1909 bp cDNA of FIG. 4 is split into Panels (A) and (B) of FIG. 4.

Figure 5:

FIG. 5 shows the fibrin autography for screening PAI activity in λPAI-75.1 transfected *E. coli* JM 105 cells. The λPAI-75.1 transfected JM 105 cells were grown at 37° in LB medium containing 50 μg/ml ampicillin to optical density (OD)=0.7. After addition of 1 mM IPTG, the cells were further incubated for 2 hrs. Aliquots of 0.8 ml of cultures were centrifuged to pellet the cells, and the cells were resuspended in μl of phosphate buffered saline (PBS). The suspensions were briefly sonicated to lyse the cells. Fifteen μl of lysates were each mixed with 5 μl of urokinase (5 CTA units/ml) and incubated for 30 min. at room temperature. Two μl each of the mixtures were spotted on a fibrin-agar plate. The clones which expressed higher level of PAI completely inhibited the urokinase induced fibrin lysis while controls and those which expressed low levels of PAI showed fibrin lysis as evident by the clear lytic zone in 6 wells.

Figure 6:
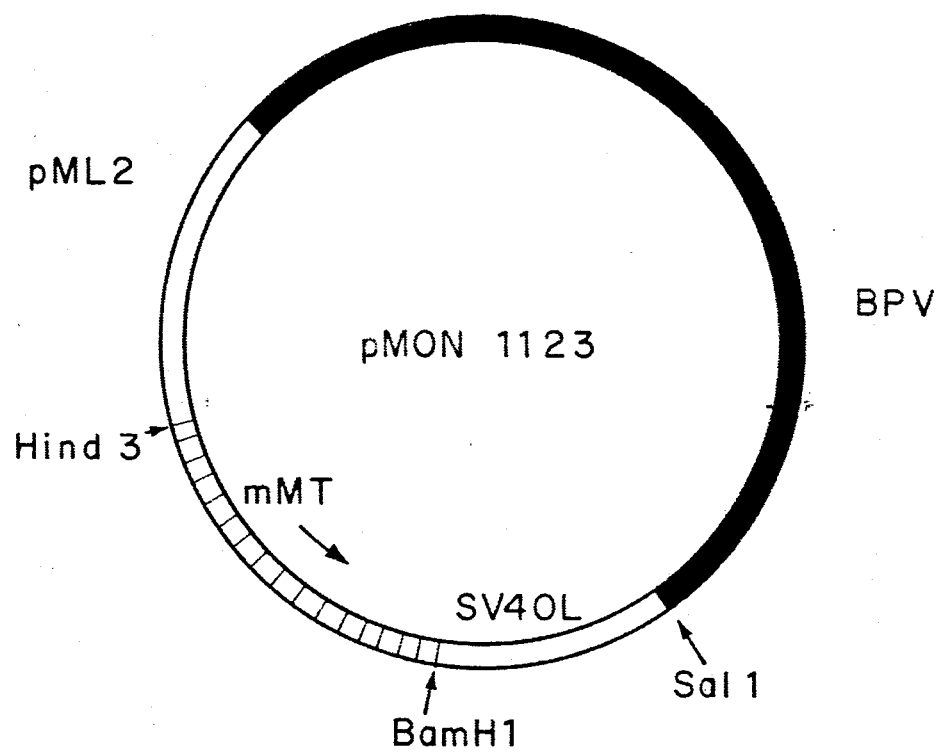

FIG. 6 is a diagrammatic representation which shows the structure of the bovine papilloma virus expression vector, pMON1123, which was used for the expression of PAI-2 protein in mouse C-127 cells in one embodiment of the invention. In this vector: BPV is the complete bovine papilloma virus genome, SV40L is the late poly(A) addition site of the SV40 virus, mMT is the mouse metallothionin I promoter, and pML2 is a derivative of the E. coli plasmid pBR322 with an animal viral insert.

Standard biochemical nomenclature is used herein in which the nucleotide bases are designated as adenine (A); thymine (T); guanine (G); and cytosine (C). Corresponding nucleotides are, for example, deoxyguanosine-5'-triphosphate (dGTP). Amino acids are shown either by three letter or one letter abbreviations as follows:

| Abbreviated Designation | | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Commonly available restriction endonuclease used herein have the following restriction sequences and (indicated by arrows) cleavage patterns:

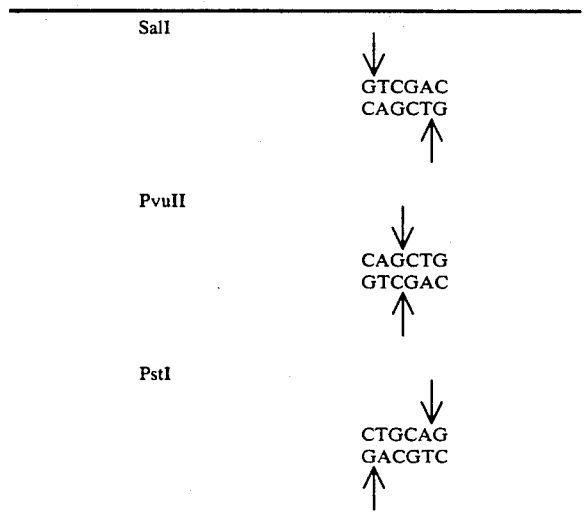

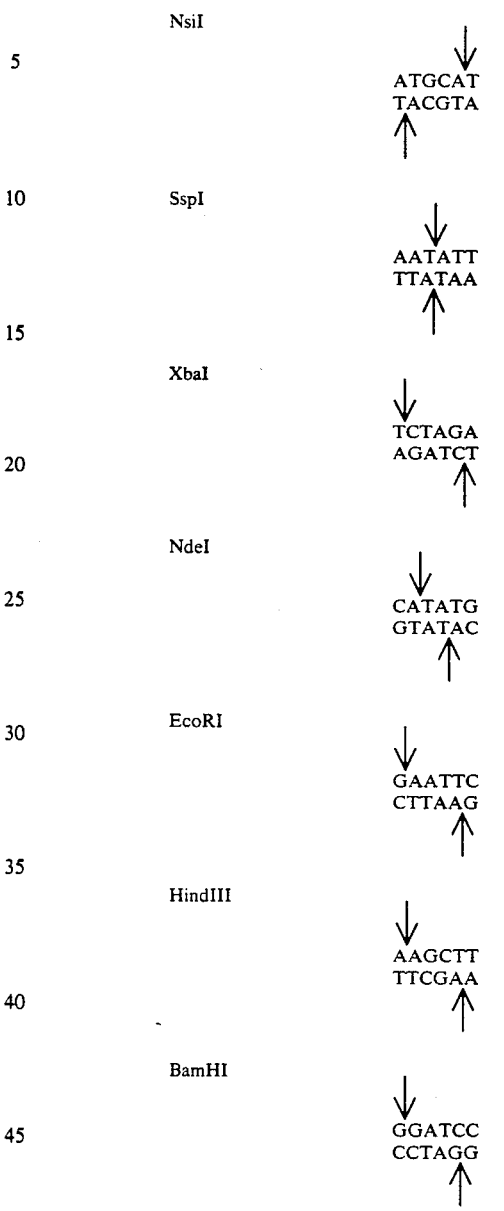

In order to illustrate specific preferred embodiments of the invention in greater detail, the following examplary laboratory preparative work was carried out. Example 1 illustrates the development of the complete coding sequence of cDNA clones representing essentially the full size PAI-2 protein. Example 2 illustrates the active recombinant PAI-2 protein expression in E. coli and mouse C-127 cells although it will be appreciated that other bacterial and mammalian cell cultures and expression vectors can be used for similar such protein expression.

EXAMPLE 1

Materials

Restriction enzymes and T4 DNA ligase were purchased from Bethesda Research Laboratories or New England Biolabs. Calf intestine alkaline phosphatase, E. coli DNA polymerase I, and S1 nuclease were purchased from Boehringer Mannheim. T4 polynucleotide kinase and exonuclease III were obtained from New England Biolabs. Mung bean nuclease, T4 DNA polymerase and the Klenow fragment of *E. coli* DNA polymerase I were purchased from Bethesda Research Laboratories. [$^{32}$P]-labeled deoxyribonucleotides and deoxyadenosine 5'-[α-$^{35}$S]thiotriphosphate ([$^{35}$S]dATPαS} were from Amersham. Nitrocellulose filters were from Schleicher and Schuell. Goat anti-rabbit IgG horseradish peroxidase conjugate and IgG beads were obtained from Bio-Rad. The IgG beads were reconstituted in 5 ml of PBS solution before use. Deoxyribonucleotides and dideoxyribonucleotides for sequencing reactions, and oligo(dT)-cellulose were purchased from Pharmacia. Bovine thrombin was obtained from Parke-Davis. Plasminogen was isolated from human plasma using lysine-Sepharose® 4B chromatography [Deutsch and Mertz, *Science* 170, 1095-1096 (1970)]. Partially purified human urokinase (Winkinase®) was from Winthrop Laboratories. Urokinase was further purified by benzamidine-Sepharose chromatography using Winkinase as starting material, as described by Wun et al., *J. Biol. Chem.* 257, 7262-7268 (1986). $^{125}$I-urokinase was prepared by a gentle chloramine T iodination method described by Wun and Capuano, Ibid 260, 5061-5066 (19B5). Phorbol 12-myristate 13-acetate and lactalbumin hydrolysate were from Sigma. Trasylol® was purchased from American Diagnostica Inc. RPMI and DME cell culture media were obtained from Gibco Laboratories. Oligonucleotides were synthesized on an Applied Biosystems Synthesizer Model 380A and purified by polyacrylamide gel electrophoresis.

Buffers

PBS is 10 mM sodium phosphate, pH 7.4, 150 mM NaCl. PBB is PBS containing 5 mg/ml bovine serum albumin (BSA) and 2.5 mg/ml bovine gamma globulin. TBS is 50 mM Tris-Cl, pH 7.9, 150 mM NaCl. TBST is TBS containing 0.05% (v/v) Tween®-20. SST is 15 mM Tris-Cl, pH 7.5, 150 mM NaCl, 2.5 mM EDTA. SSC is 0.15 M NaCl, 0.015 M sodium citrate, pH 7.0.

Preparation of cDNA Libraries

Male term placenta was flash-frozen as 1 cm dice in liquid nitrogen and stored at −70° C. Human umbilical vein endothelial cells were cultured as described by Sadler et al., *Proc. Natl. Acad. Sci.* 82, 6394–6398 (1985). Total cellular and poly(A)+ RNA was prepared from placenta and endothelial cells according to Chirgwin et al., *Biochemistry* 18, 5294–5299 (1979), as modified by Sadler et al., supra. Double stranded cDNA was synthesized from both placenta and endothelial cell poly-(A)+RNA according to Gubler and Hoffman, *Gene (Amst.)* 25, 263–269 (1983). The ends were blunted with mung bean nuclease for 5 min at 25° C. in a volume of 200 μl containing 30 mM sodium acetate, pH 4.6, 50 mM NaCl, 1 mM ZnCl$_2$, 5% (v/v) glycerol, 5.5 μg cDNA, and 150 units mung bean nuclease. Reaction was terminated by phenol/chloroform extraction and ethanol precipitation. The cDNA was then blunted again with T4 DNA polymerase for 30 min at 37° C. in a volume of 30 μl containing 33 mM Tris-Cl, pH 8.0, 10 mM magnesium acetate, 66 mM potassium acetate, 1 mM dithiothreitol, 250 μM of each deoxyribonucleotide, 0.1 mg/ml bovine serum albumin, and 3 units T4 DNA polymerase. Reaction was stopped with 1 μl 0.5 M EDTA-Na, pH 8.0, followed by phenol/chloroform extraction and ethanol precipitation. Oligonucleotide adaptors similar to those described by Wood et al., *Nature* 312, 330–337 (1984), were synthesized with the sequences:

```
5'-AATTCATCTGTCGACTGCTACC-3'
3'-  GTAGACAGCTGACGATGG-5'
    EcoRI    SalI
```

The shorter oligonucleotide was phosphorylated for 30 min at 37° C. in a reaction containing 70 mM Tris-Cl, pH 7.6, 10 mM MgCl$_2$, 5 mM dithiothreitol, 1 mM ATP, 0.5 units/μl T4 polynucleotide kinase, and 0.1 μg/μl oligonucleotide. After purification by polyacrylamide gel electrophoresis, the phosphorylated short oligonucleotide was annealed to the longer, producing a double stranded adaptor with a blunt end that could be ligated, a cohesive EcoRI terminus that could not, and a SalI site in the center of the adaptor. Six μg of annealed adaptors were ligated to 2 μg of blunt-ended cDNA in a volume of 20 μl containing 50 mM Tris-Cl, pH 7.6, 10 mM MgCl$_2$, 10 mM dithiothreitol, 1 mM ATP, and 800 units T4 DNA ligase (New England Biolabs), for 16 h at 14° C. The cDNA was extracted with phenol/chloroform and precipitated with ethanol. Products larger than 1 kb were purified by preparative electrophoresis on a 3.5% polyacrylamide gel and electroelution Maniatis et al., *Mol. Cloning: A Lab. Manual*, Cold Spring Harbor Lab., N.Y.(1982)]. The recovered size-selected and adaptor-ligated cDNA was phosphorylated with T4 polynucleotide kinase as described above in a total volume of 20 μl containing 0.3–0.4 μg cDNA. The phosphorylated cDNA was ligated to dephosphorylated λgt11 arms and packaged (Gigapack, Vector Cloning Systems, San Diego, Calif.). Twenty μg of placental poly(A)+ RNA yielded 0.4 μg of final cDNA that gave 10.5 million independent phage, of which 90% were recombinant. Twenty μg of endothelial cell poly(A)+ RNA yielded 0.6 μg of final cDNA. Packaging of 0.3 μg gave 78.3 million independent phage, of which 92% were recombinant.

Isolation of Human Placental PAI, Production of Antiserum, and Purification of Antibody Human placental PAI was purified using an 8-step procedure involving saline extraction, ammonium sulfate fractionation, column chromatography on CM-cellulose, DEAE-Sepharose and hydroxylapatite, chromatofocusing, preparative gel electrophoresis and hydrophobic chromatography, essentially as described by Wun and Reich, *J. Biol. Chem.* 262(8), 3646-3653 (1987).

Initially, a crude inhibitor fraction was obtained by saline extraction, ammonium sulfate fractionation and CM-cellulose adsorption as described by Holmberg et al., *Biochim. Biophys. Acta* 544, 128-137 (1978). The crude inhibitor was then subjected to a further 5-step procedure to isolate the inhibitor in essentially homogeneous form as follows:

Step 1: DEAE-Sepharose CL-6B chromatography

After reduction with dithiothreitol (DTT), the crude inhibitor preparation was adsorbed onto a column of DEAE-Sepharose and chromatographed using a salt gradient with 0 and 0.18 M NaCl as limiting concentrations. Most of the inhibitory activity was eluted as a single peak in the region 0.09–0.13 M NaCl. As measured by the L-pyroglutamyl-glycyl-L-arginine-p-nitroanilide (S2444) annidolytic assay, about 12% of the initial inhibitor was not adsorbed initially and passed directly through the column; this material was not characterized further.

Step 2: Hydroxylapatite chromatography The peak fractions from the DEAE-Sepharose column were pooled, dialysed against 0.01 M sodium phosphate buffer, pH 6.8, containing 0.05% β-mercaptoethanol (βME), and loaded onto a column of hydroxylapatite. After washing the column, the proteins were eluted with a phosphate buffer gradient, pH 6.8, (0.01–0.11 M NaPO$_4$). Most of the inhibitory material appeared as a single peak which was eluted from the column in the region 0.03–0.07 M NaPO$_4$.

Step 3: Chromatofocussing

The most active fractions obtained from the hydroxylapatite column were pooled, dialysed, and then fractionated by chromatofocussing on PBE-94 gel (Pharmacia, Inc.). Essentially all of the inhibitory activity was recovered in a single peak in the pH range 5.1–4.6. The elution pH range in this procedure was identical with the pI obtained by isoelectric focussing with ampholines in a flat bed of Sephadex G-75 gel (data not shown).

Step 4 Preparative polyacrylamide gel electrophoresis

The active material obtained from chromatofocusfocussing was transferred into a dialysis bag which was embedded in Aquacide until enough solvent had been removed to reduce the volume from 10.8 ml to 3 ml. The concentrated solution was then fractionated further by electrophoresis through a polyacrylamide gel column using the Savant preparative gel electrophoresis system. The sample (1.5 ml aliquot) was prepared in 10% glycerol, 20 mM Tris-HCl, pH 8, 0.05% βME, 20 mM DTT containing tracer bromophenol blue and applied onto a 4-ml column of 10% polyacrylamide gel overlaid with 2 ml of 4% polyacrylamide stacking gel, in a 1×11 cm column. The Laemmli gel buffer system, Nature 227, 680–685 (1970), was used except that all buffers contained 0.05% βME and no SDS was present. Electrophoresis was carried out at room temperature. An initial potential of 75 volts was applied until the protein entered the separating gel. Then the voltage was raised to 125 volts and the proteins were continuously collected from the elution chamber using a peristaltic pump. Fractions of 1.2 ml were collected every 12 min. The position of the inhibitor was located both by inhibition of uPA in the S2444 assay and by analytical SDS-PAGE. The inhibitor was found in fractions 16 to 26 after the appearance of bromophenol blue.

Step 5: Phenyl-Sepharose chromatography

The inhibitor pool obtained from the preparative PAGE was again concentrated to a final volume of 2 ml by means of Aquacide, dialyzed against 10 mM HEPES, pH 8.0, 0.05% βME, and adsorbed onto a 0.6×7 cm phenyl-Sepharose column. The column was then washed with 20 ml of the same buffer at 4°, and the inhibitor was eluted with a buffer containing 50% ethylene glycol, 10 mM HEPES, pH 8.0, and 0.05% βME at room temperature.

The purified inhibitor had a molecular mass of 47,000 daltons by SDS-polyacrylamide gel electrophoresis (SDS-PAGE) [Laemmli, Nature 227, 680–685 (1970)]and formed a 1:1 complex with urokinase. Antiserum against the placental PAI was raised in rabbits by immunization with purified inhibitor. New Zealand white rabbits were treated initially with 100 μg of purified inhibitor suspended in 2 ml of complete Freunds' adjuvant, injected directly into popliteal lymph nodes, subcutaneous sites and the peritoneal cavity. Booster injections of 50 μg inhibitor in incomplete Freunds' adjuvant were administered 5 weeks later. Rabbits were bled weekly beginning at 6 weeks and boosted every month. Specific antibody against the placental inhibitor was purified by affinity chromatography on a placental inhibitor-Sepharose 4B column. The placental inhibitor-Sepharose 4B column was prepared by coupling ~0.8 mg of purified inhibitor to 0.5 g of cyanogen bromide activated Sepharose 4B (Pharmacia) according to the manufacturer's published recommended procedure. Antiserum (3 ml) was mixed with equal volume of PBS supplemented to 0.4 M NaCl, 0.1 M benzamidine, and 1% (v/v) Triton ® X-100 and applied to the placental inhibitor-Sepharose 4B column. The column was washed with 20 ml of column buffer and then with 20 ml of column buffer without Triton X-100. Specific antibody was eluted from the column with 0.1 M glycine-HCl, pH 2.2, immediately neutralized with 1/10 volume of 1 M Tris-OH, and dialyzed against 0.15 M NaCl. Each chromatography yielded approximately 2 mg of antibody.

Screening of λgt11 cDNA Libraries

Human placenta and endothelial cell cDNA libraries were screened as described by Sadler et al., Proc. Natl. Acad. Sci. USA 82, 6394–6398 (1985), and Young and Davis, Science 222, 778–782 (1983). Affinity-purified rabbit anti-human placental PAI antibody was used at a concentration of 2 μg/ml in TBST. Bound antibody was detected with horseradish peroxidase conjugated to goat anti-rabbit IgG [deWet et al., DNA(NY) 3, 437–447 (1984)]. Positive isolates were plaque purified and DNA prepared from plate lysates [Helms et al., Ibid. 4, 39–49 (1985)]. The cDNA insert of λPAI-75.1 was labeled with [α-$^{32}$P]dCTP by nick translation [Maniatis et al., supra.] and employed to screen both cDNA libraries according to Benton and Davis, Science 196, 180–182 (1977). The 14 positives obtained among 300,000 recombinants of the placenta cDNA library were screened with an oligonucleotide corresponding to the complement of λPAI-75.15 residues −42 to −25. The oligonucleotide was labeled with [Y-$^{32}$P]dATP and T4 polynucleotide kinase [Maniatis et al., supra.]to a specific activity of at least $10^8$ cpm/μg. Filters were prehybridized in 180 mM Tris-Cl, pH 7.5, 0.9 M NaCl, 12 mM EDTA, 2×Denhardt×s solution, and 10 μg/ml denatured salmon sperm DNA. Hybridization was performed in 7 ml of prehybridization buffer per 82 mm filter containing $2.5 \times 10^5$ cpm/ml of probe at 46° C. for 12 h. The final wash condition was in 2×SST at 43° C. for 20 minutes.

DNA Sequence Analysis

The cDNA inserts of λPAI-75.1 and λPAI-75.15 were subcloned in both orientations into the EcoRI or SalI site of M13mp19 or M13mp18 (cloning vehicles from bacteriophage M13). Deletions were generated using exonuclease III [Henikoff, Gene (Amst.) 28, 357–359(1984)]. Nucleotide sequence was determined by the dideoxy method of Sanger et al., Proc. Natl. Acad. Sci. USA 74, 5463–5467(1977), using [$^{35}$S]dATPαS and buffer-gradient gels Biggin et al., Ibid. 80, 3963–3965 (1983)].

Preparation of λ-phage Lysates Containing Recombinant Proteins

Each plaque purified λgt11 isolate or λgt11 was with E. coli Y1090 in 8 ml LB-0.7% agar onto 15 cm LB-agar plates at a density of 50,000 pfu/plate [Maniatis et al., supra.]Expression of recombinant proteins was induced by isopropyl β-D-thiogalactoside (IPTG) which was added to 1.25 mM in the top agar. After 12 hours at 37° C., 10 ml of TBS was added to each plate and incubated 12 hours at 4° C. with gentle agitation. The lysate was recovered and bacterial debris was removed by centrifugation.

Fibrin Autography Assay for PAI Activity of Recombinant proteins

The λ-lysates containing recombinant proteins were screened for inhibitory activity against urokinase using a fibrin-agar plate spot assay. The fibrin-agar plate was prepared by mixing 2.5 ml of 2×PBS, 36 µl of 100 units/ml bovine thrombin, 68 µl of 3 mg/ml plasminogen, 5.5 ml of 2.5% agarose, and 2.5 ml of 10 mg/ml fibrinogen at 48° C., then pouring the solution onto a 90 mm plastic petri dish. For the pot assay, 45 µl of λ-lysate was treated with 3 µl of anti-placental PAI immunoglobulin (0.5 mg/ml) or 3 µl of normal rabbit immunoglobulin (0.5 mg/ml) at 4° C. for 1 h. Then 5 µl urokinase solution was added (5 CTA units of Winkinase/ml PBB). After incubation at room temperature for 30 minutes, 2 µl of the solution was spotted onto the fibrin-agar plate and the plate was incubated in a humidified box at 37° C. overnight. Urokinase activity was measured by the appearance of a lytic zone and PAI activity was detected by abolishment of the lytic activity.

SDS-PAGE Assay of Complex Formation between $^{125}$-urokinase and Recombinant Proteins Expressed by λ-phage Isolates Aliquots (0.1 ml) of λ-lysates or PBB buffer were mixed with 5 µl of $^{125}$I-urokinase (53 CTA units/ml) and incubated at room temperature for 30 minutes. Three µl of anti-placental inhibitor IgG (0.2 mg/ml in PBS) was added and the mixture was incubated at 4° C. overnight. Twenty-five µl of goat anti-rabbit immunoglobulin beads (Bio-Rad, each vial was reconstituted in 5 ml of PBB solution) was added and the mixture was incubated for 2.5 hours at room temperature. The beads were collected by centrifugation and washed twice with 1 ml of PBS supplemented to 0.4 M NaCl, 0.1 M benzamidine and 1% (v/v) Triton X-100 and then washed twice with 1 ml of water. Buffer (30 µl) containing 0.1 M glycine-HCl, pH 2.2, 0.1% (w/v) SDS, 0.001% (w/v) bromphenol blue, 20 mM dithiothreitol and 6 M urea was added to the washed beads and the suspensions were incubated at 37° C. for 30 minutes to release the bound material The suspensions were then centrifuged and 25 µl of the supernatant was used for SDS-PAGE in a 7.5% polyacrylamide gel [Laemmli, supra.]. The gel was fixed and dried for autoradiography.

Affinity Purification of Antibodies upon λgt11 Recombinant Proteins

This procedure is adapted from Weinberger et al., Science 228, 740–746 (1985). Recombinant proteins from positive λ-phage isolates or from λgt11 were plated on E. coli Y1090 at 50,000 pfu/15 cm plate of LB-agar in 10 ml LB-0.7% agar and incubated 3 h at 42° C. The soft agar was overlaid with nitrocellulose filters saturated with 10 mM IPTG and incubated at 37° C. for 12 h. The filters were removed and incubated in TBST containing 3% (w/v) BSA for 1 h, then incubated with affinity-purified rabbit anti-human placental PAI antibody at a concentration of 2 µg/ml in TBST at 4° C. for 12 hours. Filters were rinsed three times for 5 min each in TBS containing 1 mM EDTA-Na. Bound antibodies were eluted from the filters with two 5 ml [aliquots of 4 M MgCl$_2$, 50 mM Tris-Cl, pH 7.5, 0.5% (w/v) BSA, for 5 min each wash. The eluted antibodies were dialyzed against 3 changes of TBST, 1 liter each, at 4° C. for 2 hours each change. The dialyzed solutions were used directly to detect purified placenta PAI spotted onto nitrocellulose filters in 1 µl of TBS containing 0.05 ng, 0.15 ng, 0.5 ng, 2.5 ng, and 5.0 ng PAI protein. Conditions for this assay were as described under *Screening of λgt11 cDNA libraries*, above.

Culture of U-937 and HepG2 Cells and Preparation of RNA

U-937 cells were grown at 37° C. in RPMI supplemented with 10% fetal bovine serum in 150 cm$^2$ culture flasks until the cell density reached approximately $1 \times 10^6$ cells/ml. The cells were washed twice with PBS and resuspended at a density of $\sim 2 \times 10^6$ cells/ml in RPMI supplemented with 0.5% (w/v) lactalbumin hydrolysate and 50 U/ml Trasylol, or in the same medium plus 1 µM PMA. The cells were then incubated further for 18 hours. HepG2 cells were grown at 37° C. in DME supplemented with 10% fetal bovine serum in 150 cm$^2$ culture flasks to confluency. Poly(A)+ RNA was prepared as described under *Preparation of cDNA libraries*, above.

Northern Blot Analysis

Five µg of each RNA sample was subjected to agarose gel electrophoresis in buffer containing formaldehyde and transferred to nitrocellulose [Maniatis, supra.]. Standards included bovine liver 28S and 18S RNA, and HindIII fragments of λ-phage DNA. The insert of λPAI-75.1 or a cDNA insert for human γ-actin was labeled by nick translation as described under *Screening of λgt11 cDNA libraries*, above, and the blot was hybridized in 50 ml of 50% formamide, 6×SSC, 25 mM HEPES, pH 7.0, 25 µg/ml denatured salmon sperm DNA, 1×Denhardt's solution, 0.1% (w/v) SDS, 1 mM EDTA and 10% dextran sulfate, containing $1 \times 10^7$ cpm of probe at 42° C. for 16 hours. The filter was washed in 0.1×SSC, 0.1% SDS at 42° C. for 15 minutes, and then at 68° C. for 30 minutes. Kodak XAR-5 film was exposed with the wet filter at −70° C. for 10 hours with an intensifying screen.

Protein Sequence Alignment and Computer Analysis

The sequences of individual members of the serpin family were aligned by visual inspection and with the assistance of the ALIGN computer program [Dayhoff et al., *Methods Enzymol.* 91, 524–545 (1983)]. Previously published alignments were also consulted [Bock et al., *Biochemistry* 25, 4292–4301 (1986), and Carrele et al. in *Protease Inhibitors*, Barrett and Salvesen, eds., Elsevier/North-Holland Biomed. Press, 1986)]. Phylogeny of sequences was determined by considering the percentage of difference between sequences and alignment scores using either the mutation data matrix or the unitary matrix for the alignment shown in Table I, using the parsimony principle. Sequences amino-terminal to helix A of α$_1$-antitrypsin [Loebermann et al., *J. Mol. Biol.* 177, 531–556 (1984)] were not included in this analysis. The hydropathy or hydrophilicity profiles of placental PAI were calculated using the methods of Hopp and Woods, *Proc. Natl. Acad. Sci. USA* 78, 3824–3828 (1981), and Kyte and Doolittle, *J. Mol. Biol.* 157, 105–132 (1982).

The alignment of placental PAI with other serpins is shown in the following Table I.

TABLE I

```
                                                                              m
ATIII, human:                          GSKGPLDQLEKGGETAQSADPQWEQ
HCII, human:
Clinh, human:   masrltlltllllllagdrassNPNATSSSSQDPESLQDRGEGKVATTVISKMLFVEPIL
AGTH, human:                   mrkrapqsemapagvslratilcl
AGTH, rat:                     mtptgaglkatifci 1
ECPAI, human:                                  mqmspaltc
α1AT, human:                       mpssvswgillllaglcclvpvslaEDPQ
α1AT, baboon:                            /lllaglccllpgslaEDPQ
α1 ACT, human:                    mermlpllalgllaagfcpavlchpNS
ATIII, human:    ysnvigtvtsgkrkvyllsllligfwdcytcHGSPVDICTAKPRDIPMNPMCIYRSPEKK
HCII, human:     LNNKNLSMPLLPADFHKENTVTNDWIPEGEEDDDYVDICTAKPRDIPMNPMCIYRSPEKK
Clinh, human:    EVSSLPTTNSTTNSATKITANTTDEPTTQPTTEPTTQPTIQPTQPTTQLPTDSPTQPTTG
AGTH, human:     lawaglaagDRVYIHPFHLVIHNESTCEQLAKANAGKPKDPTFIPAPIQAKTSPVDEKAL
AGTH, rat:       ltwvsltagDRVYIHPFHLLYYSKSTCAQLENPSVETLPEPTFEPVPIQAKTSPVDEKTL 10·       20         30        40          50         60
                          [         helix A         ]   [ s6B ] [   helix B
PPAI, human:          MEDLCVANNTLFALNLFKHLAKASPT - QNL - FLSPWSISSTMA
Oval, chicken:          mGSIGAASMEFCFDVFKELKVHHAN - ENI - FYCPIAIMSALA
GeneY, chicken:       MDSISVTNAKFCFDVFNEMKVHHVN - ENI - LYCPLSILTALA
ECPAI, human:    lvlglalvfgegsaVHHPPSYVAHLASDFGVRVFQQVAQASKDR - NV - VFSPYGVASVLA
α1At, human:     GDAAQKTDTSHHDQDHPTFNKITPNLAEFAFSLYRQLAHQSNS - TNI - FFSPVSIATAFA
α1At, baboon:    GDAAQKTDTPPHDQNHPTLNKITPSLAEFAFSLYRQLAHQSNS - TNI - FFSPVSIATAFA
α1ACT, human:    PLDEENLTQENQDRGTHVDLGLASANVFAFSLYKQLVLKALD - KNV - IFSPLSISTALA
ATIII, human:    ATEDEGSEQKIPEATNRRVWELSKANSRFATTFYQHLADSKNDNDNI - FLSPLSISTAFA
HCII, human:     DSDVSAGNILQLFHGKSRIQRLNILNAKFAFNLYRVLKDQVNTFDNI - FIAPVGISTAMG
Clinh, human:    SFCPGPVTLCSDLESHSTEAVLGDALVDFSLKLYHAFSAMKKVETNMA - FSPFSIASLLT
AGTH, human:     QDQLVLVAAKLDTEDKLRAAMVGMLANFLGFRIYGMHSELWGVVHGATVLSPTAVFGTLA
AGTH, rat:       RDKLVLATEKLEAEDRQRAAQVAMIANFMGFRMYKMLSEARGVASGA - VLSPPALFGTLV
Consensus:                          ++ +++ FAF LY+ L           NI  F+SP+SI +TALA 70        80
                 ]   [    helix C    ]                                  [
PPAI, human:     MVYMGSRGSTEDQMAKVLQFNEVGANAVTPMTPENFTSCGFMQQIQKGSYPDAILQAQAA
Oval, chicken:   MVYLGAKDSTRTQINKVVRFDKLP - - - - - - - - - - - - - - - - - - - - - - - - - GFGDSIEAQCGTS
GeneY, chicken:  MVYLGARGNTESQMKKVLHFDSIT - - - - - - - - - - - - - - - - - - - - - - - - - GAGSTTDSQCGSS
ECPAI, human:    MLQLTTGGEQQQIQAAMGFKIDD - - - - - - - - - - - - - - - - - - - - - - - - - - KGMA
α1AT, human:     MLSLGTKADTHDEILEGLNFN - LT - - - - - - - - - - - - - - - - - - - - - - - - - - - - - EIPE
α1AT, baboon:    MLSLGTKADTHSEILEGLNFN - LT - - - - - - - - - - - - - - - - - - - - - - - - - - - - - EIPE
α1ACT, human:    FLSLGAHNTTLTEILKASSSP - HG - - - - - - - - - - - - - - - - - - - - - - - - - - - - - DLLR
ATIII, human:    MTKLGACNDTLQQLMEVFKFDTIS - - - - - - - - - - - - - - - - - - - - - - - - - - - - EKTS
HCII, human:     MISLGLKGETHEQVHSILHFKDFV - - - - - - - - - - - - - - - - - - - - - - - - - - - - NASSKYEI
Clinh, human:    QVLLGAGQNTKTNLESILSYP - KD - - - - - - - - - - - - - - - - - - - - - - - - - - - - - FTCV
AGTH, human:     SLYLGALDHTADRLQAILGVPWKD - - - - - - - - - - - - - - - - - - - - - - - - - KNCTSRLDAH - KV
AGTH, rat:       SFYLGSLDPTASQLQVLLGVPVKE - - - - - - - - - - - - - - - - - - - - - - - - - GDCTSRLDGH - KV
Consensus:       M++LG+ + T  Q+  +L F+                                   -

90       100        110       120         130        140
                 helix D  ]            [   sheet 2A   ]  [   helix E    ][ sht 1A  ]
PPAI, human:     DKIHSSFRSLSSAINASTGD - - YLLESVNKLFGEKSASFREEYIRLCQKYYSSE - PQAVD
Oval, chicken:   VNVHSSLRDILNQITKPNDV - - YSFSLASRLYAEERYPILPEYLQCVKELYRGG - LEPIN
GeneY, chicken:  EYVHNLFKELLSEITRPNAT - - YSLEIADKLYVDLTFSVLPEYLSCARKFYTGG - VEEVN
ECPAI, human:    PALRHLYKELMGPWNKD - - - - - - - EISTTDAIFVQRDLKLVQGFMPHFFRLRST - VLQVD
α1AT, human:     AQIHEGFQELLRTLNQPDSQ - - LQLTTDGGLFLSEGLKLVDKFLEDGVKKLYHSE - AFTVN
α1AT, baboon:    AQVHEGFQELLRTLNKPDSQ - - LQLTTGNGLFLNKSLKVVDFLEDVNKLYHSE - AFSVN
α1ACT, human:    QKFTQSFQHLRAPSISSSDE - - LQLSMGNAMFVKEQLSLLDRFTEDAKRLYGSE - AFATD
ATIII, human:    DQIHFFFAKLNCRLYRKANK - - SSKLVSANRLFGDKSLTFNETYQDISELVYGAK - LQPLD
α2AP, human:                                                                /PVS
HCII, human:     TTIHNLFRKLTHRLFRRN - - FGYLTRSVNDLYIQKQFPILLDFKTKVREYYFAE - AQIAD
Clinh, human:    HQALKGFTTKGVTSVSQ - - - - - - - - - - - - - - - IFHSPDLAIRDTFVNASRTLYSS - PR - - V
AGTH, human:     LSALQAVQGLLVAQGRADSQAQLLLSTVVGVFTAPGLHLKQPFVOGLALYTPVVLPRSLD
AGTH, rat:       LTALQAVQGLLVTQGGS SSQTPLLQSTVVGLFTAPGLRLKQPFV ESLGPFTPAIFP R S LD
Consensus:       +H++F++LL       +++         +L      + LF +    L + +F++   + LY S  ++++D 150      160         170       180         190        200
                 [     helix F    ]                        [      sheet 3A    ]
PPAI, human:     FL - ECAEEARKK - INSWVKTQTKGKIPNLLPEGSVDGDTRMVLVNAVYFKGKWKTPFEKK
Oval, chicken:   FQ - TAADQAREL - INSWVESQTNGIIRNVLQPSSVDSQTAMVLVNAIVFKGLWEKAFKDE
GeneY, chicken:  FK - TAAEEARQL - INSWVEKETNGQIKDLLVSSSIDFGTTMVFINTIYFKGIWKIAFNTE
ECPAI, human:    FS - E - VERARFI - INDWVKTHTKGMISNLLGKGAVDQLTRLVLVNALYFNGQWKTPFPDS·
α1AT, human:     FG - D - TEEAKKQ - INDYVEKGTQGKIVDLV - - KELDRDTVFALVNYIFFKGKWERPFEVK
α1AT, baboon:    FE - D - TEEAKKQ - INDYVEKGTQGKVVDLV - - KELDRDTVFALVNYIFFKGKWERPFEVE
α1AT, mouse:                                                   /SPANYILFKGKWKKPFDPE
α1ACT, human:    FQ - D - SAAAKKL - INDYVKNGTRGKITDLI - - KDPDSQTMMVLVNYIFFKAKWEMPFDPQ
Ctspn, mouse:                                                  /VVLVNYIYFKGKWKISFDPQ
ATIII, human:    FK - ENAEQSRAA - INKWVSNKTEGRITDVIPSEAINELTVLVLVNTIYFKGLWKSKFSPE
α2AP, human:     LT - G - KQEDDLANIQWVKEATEGKIQEF/              /SLKFDPS
HCII, human:     FS - DPAFISKTN - - NHIM - KLTKGLIKDAL - - ENIDPATQMMILNCIYFKGSWVNKFPVE
Clinh, human:    LS - N - NSDANLELINTWVAKNTNNKISRLL - - DSLPSDTRLVLLNAIYLSAKWKTTFDPK
AGTH, human:     F - TE - LDVAAEK - IDRFMQAVTGWKTGCSL - - MGASVDSTLAFNTYVHFQGKM - KGFSLL
```

TABLE I-continued

| | |
|---|---|
| AGTH, rat: | LSTD - PVLAAQK - INRFVQAVTGWKMNLPL - - EGVSTDSTLFFNTYVHFQGKM - RGFSQL |
| ProZ, barley: | /WV - EQVTXGL - IXE I LPP/ / WQK - FDEX |
| Consensus: | F + + A+ IN+WV+ T+GKI +LL ++D DT +VLVNYIYFKGKW+ +F+ + |

```
                    210       220         230        240           250
                                   [ sheet 3C  ] [sht1B] [ sheet 2B ]   [ sheet 3B
PPAI, human:     LNGLYPFRVNSAQRTPVQMMYLREKL - NIGYIEDLK - - - AQILELPYA - - - - - GDVSMFL
Oval, chicken:   DTQAMPFRVTEQESKPVQMMYQIGLF - RVASMASEK - - - MKILELPFAS - - - - GTMSMLV
GeneY, chicken:  DTREMPFSMTKEESKPVQMMCMNNSF - NVATLPAEK - - - MKILEPYAS - - - - GDLSMLV
ECPAI, human:    STHRRLFHKSDGSTVSVPMMAQTNKF - NYTEFTTPDGHYYDILELPYHG - - - - DTLSMFI
α1AT, human:     DTEEEDFHVDQVTTVKVPMMKRLGMF - NIQHCKKLS - - - SWVLLMKYLG - - - - NATAIF
α1AT, baboon:    ATEEEDFHVDQATTVKVPMMRRLGMF - NIYHCEKLS - - - SWVLLMKYLG - - - - - NATAIF
α1AT, mouse:     NTEEAEFHVDESTTVKVPMMTLSGML - DVHHCSTLS - - - SWVLLMDYAG - - - - NATAVF
α1ACT, human:    DTHQSRFYLSKKKWVMVPMMSLHHLTIPYFRDEELS - - - CTVVELKYTG - - - - - NASALF
Ctpsn, mouse:    DTFESEFYLDEKRSVKVPMMKMKLLTTRHFRDEELS - - - CSVLELKYTG - - - - - NASALL
ATIII, human:    NTRKELFYKADGESCSASMMYQEGKF - RYRRVAE - G - - - TQVLELPFKG - - - - DDITMVL
α2AP, human:     LTQRDSFLHDEQFTVPVEMMQARVYP/
HCII, human:     MTHNHNFRLNEREVVKVSMMQTKGNF - LAANDQELD - - - CDILQLEYVGG - - - - - ISMLI
C1inh, human:    KTRMEPFHFKNS - VIKVPMMDSKKYPVAHFIDQTLK - - - AKVGQLQLSH - - - - - NLSLVI
AGTH, human:     - AEPQEFWVDNSTSVSVPMLSGMGTF - - QHWSDIQD - - - NFSVTQVPFT - - - - ESACLLL
AGTH, rat:       - TGLHEFWVDNSTSVSVPMLSGTGNF - - QHWSDAQN - - - NFSVTRVPLG - - - - ESVTLLL
ProZ, barley:    N/                     /LTKKQYISSSDN - - - LKVLKLPYAKGHDKRQFSMY I
Consensus:       T++  F  +++     +V VPMM   G F           L+       VL+L Y G       + S+++

260          270          280         290          300
                         [ helix G  ] [ helix H  ]             [ sht 2C ] [ sheet 6A  ] [ helix I
PPAI, human:     LLPDEIADVSTGLELLESEITYDKLNKWTSKDKMAEDEVEVYIPQFKLEEHYEL - RSILR
Oval, chicken:   LLPDEVS - - - - GLEQLESIINFEKLTEWTSSNVMEERKIKVYLPRMKMEEKYNL - TSVLM
GeneY, chicken:  LLPDEVS - - - - GLERIEKTINFDKLREWTSTNAMAKKSMKVYLPRMKIEEKYNL - TSILM
ECPAI, human:    AAPYEKE - - - VPLSALTNILSAQLISHWKGNM - - TRLPRLLVLPKFSLETEVDL - RKPLE
α1AT, human:     FLPDEGK - - - - - LQHLENELTHDIITKFLENE - - DRRSASLHLPKLSITGTYDL - KSVLG
α1AT, baboon:    FLPDEGK - - - - - LQHLENELTHDIITKFLENE - - NRRSANLHLPKLAITGTYDL - KTVLG
α1AT, mouse:     LLPDDGK - - - - - MQHLEQTLSKELISKFLLNR - - RRRLAQIHFPRLSISGEYNL - KTLMS
α1ACT, human:    ILPDQDK - - - - - MEEVEAMLLPETLKRWRDSLEF - REIGELYLPKFSISRDYNL - NDILL
Ctpsn, mouse:    ILPDQGR - - - - - MQQVEASLQPETLRKWRKTLF - PSQIEELNLPKFSIASNYRLEEDVLP
ATIII, human:    ILPKPEK - - - - - SLAKVEELTPEVLQEWLDEL - - EEMMLVVHMPRFRIEDGFSL - KEQLQ
HCII, human:     VVPHKMS - - - - GMKTLEAQLTPRVVERWQKSM - - TNRTREVLLPKFKLEKNYNL - VESKL
C1inh, human:    LVPQNLK - - - HRLEDMEQALSPSVFKAIMEKLEMSK - FQPTLLTLPRIKVTTSQDMLSIM
AGTH, human:     IQPHYASD - - - - LDKVEGLTFQQNSLNWMKKL - - SPRTIHLTMPQLVLQGSYDL - QDLLA
AGTH, rat:       IQPQCASD - - - - LDRVEVLVFQHDFLTWIKNP - - PPRAIRLTLPQLEIRGSYNL - QDLLA
ProZ, barley:    LLPGAQD - - - - GLWSLAKRLSTEPEFIENH I PKQTVEVGRFQLPKFKISYQFEA - SSLLR
Consensus:        +LPD+          L++LE   L+ + +  W    +    +  R   ++LP++   I   Y+L   + +L 310           320          330           340             350
                                                                  [ sheet 5A   ] [  sheet 4A          ]
PPAI, human:     SMGMEDAFNKGRAN - FSGMSERN - - DLFLSEVFHQAMVDVNEEGTEAAAGTGGVMTG - RT
Oval, chicken:   AMGITDVFSSS - AN - LSGISSAE - - SLKISQAVHAAHAEINEAGREVVGSAEAGVDA - AS
GeneY, chicken:  ALGMTDLFSRS - AN - LTGISSVD - - NLMISDAVHGVFMEVNEEGTEATGSTGAIGNIKHS
ECPAI, human:    NLGMTDMFRQFQAD - FTSLSDQE - - PLHAQALLQKVKIEVNESGTVASSSTAVIVSA - RM
α1AT, human:     QLGITKVFSNG - AD - LSGVTEEA - - PLKLSKAVHKAVLTIDEKGTEAAGAMFLEAIP - MS
α1AT, baboon:    HLGITKVFSNG - AD - LSGVETDA - - PLKLSKAVHKAVLTIDEKGTEAAGAMFLEAIP - MS
α1AT, mouse:     PLGITRIFNNG - AD - LSGITEENA - PLKLSQAVHKAVLTIDETGTEAAAVTVLLAVP - YS
α1ACT, human:    QLGIEEAFTSK - AD - LSGITGAR - - NLAVSQVVHKVVSDVFEEGTEASAATAVKITL - LS
Ctpsn, mouse:    EMGIKEVFTEQ - AD - LSGIIETK - - KLSVSQVVHKAVLDVAETGTEAAAATGVIGGIRKA
ATIII, human:    DMGLVDLFSPEKSK - LPGIVAEGRDDLYVSDAFHKAFLEVNEEGSEAAASTAVVIAG - RS
HCII, human:     LMGIRMLFDKN - GNMAGISDQRIAIDLFK - - - - HQGTITVNEEGTQATTVTTVGFMP - LS
C1inh, human:    EKLEFFDFSYD - LN - LCGLTEDP - - DLQVSAMQHQTVLELTETGVEAAAASAISVA - - RT
AGTH, human:     QAELPAILHTE - LN - LQKLSNDR - - - IRVGEVLNSIFFEL - EADERE - PTESTQQ - L - NK
AGTH, rat:       QAKLSTLLGAE - AN - LGKMGDTN - - P - RVGEVLNSILLEL - QAGEEEQPTSAQQ - P - GS
ProZ, barley:    ALGLQLPFSEE - AD - LSEMVDSS - QGLE I SHVFHKS F VEVNEEGTEAG AA TVAMGVA - MS
Consensus:        +G+   +F++  A+  LSG+++        L  +S+  +HK+++EV+E GTEA+++T+           +     S 360         370         380            390  394
                         [ sheet 1C ] [ sheet 4B ] [ sheet 5B ]
PPAI, human:     GHGGPQ - - - FVADHPFLFLIMHKITKCILFFGRFCSP
Oval, chicken:   VS - EE - - - - FRADHPFLFCIKHIATNAVLFFGRCVSP
GeneY, chicken:  LELEE - - - - FRADHPFLFFIRYNPTNAILFFGRYWSP
ECPAI, human:    AP - EE - - - - IIMDIPFLFVVRHNPTGTVLFMGQVMEP
α1AT, human:     IPPE - - - - - VKFNKPFVFLMIEQNTKSPLFMGKVVNPTQK
α1AT, baboon:    IPPE - - - - - VKFNKPFVFLMIEQNTKSPLFIGKVVNPTQK
α1AT, mouse:     MPPI - - - - - LRFDHPFLFIIFEEHTQSPLFVGKVVDPTHK
α1ACT, human:    ALVET - RTIVRFNRPFLMIIVTDTQNIFFMSKVTNPSKPRACIKQWGSQ
Ctpsn, mouse:    ILPA - - - - - VHFNRPFLFVIYHTSAQSILFMAKVNNPK
ATIII, human:    LNPN - - RVTFKANRPFLVFIREVPLNTIIFMGRVANPCVK
HCII, human:     - - - - - TQVRFTVDRPFLFLIYEHRTSCLLFMGRVANPSRS
C1inh, human:    LLV - - - - - - FEVQQPFLFVLWDQQHKFPVFMGRVYDPRA
AGTH, human:     PEVLE - - - - FVTLNRPFLFAVYDQSATALHFLGRVANPLSTA
AGTH, rat:       PEVLD - - - - VTLSSPFLFAIYERDSGALHFLGRVDNPQNVV
ProZ, barley:    MPLKVDLVDFVANHPFLFLIREDIAGVVVFVGHVTNPLISA
Consensus:                 + +++PFLF+I ++ T+++LF+GRV NP
```

In the above table, sequences of human antithrombin III (ATIII), human and rat angiotensinogen (AGTH), human and baboon $\alpha_1$-antitrypsin ($\alpha$IACT), ovalbumin (Oval), and chicken gene Y protein (Gene Y) were obtained from the National Biomedical Research Foundation Protein Sequence Database (Georgetown University, Washington, D.C., Release 9.0, May 28, 1986), except that threonine was substituted for residue 249 of $\alpha_1$-antitrypsin [Kurachi et al., *Proc. Natl. Acad. Sci. USA* 78, 6826–6830 (1981)]. Sequences of mouse $\alpha_1$-antitrypsin and contrapsin (Ctpsn) were translated from the Genbank Genetic Sequence Bank (BBN Laboratories Inc., Cambridge, MA, Release 42.0, May 2, 1986). Endothelial cell PAI-1 (ECPAI), [Ny et al., *Proc. Natl. Acad. Sci. USA* 83, 6776–6780 (1986), Pannekoek et al., *EMBO J.* 5, 2539–2544 (1986), and Ginsburg et al., *J. Clin. Invest.* 78, 1673–1680 (1986)], heparin cofactor II (HCII) [Ragg, *Nucleic Acids Res.* 14, 1073–1088 (1986)], $\alpha_2$-antiplasmin ($\alpha$2AP) Lijnen et al., *Thromb. Haemostasis* 48, 311–314 (1982)], Cl-esterase inhibitor (Clinh) [Bock et al., supra] and barley protein Z (ProZ) [Hejgaard et al., *FEBS Lett.* 180, 89–94 (1985)] were obtained from the directly indicated references. Dashes (---) represent gaps introduced to optimize alignment. Slashes (/) indicate the boundaries of incomplete sequences. The positions of $\alpha$-helices and the strands of $\beta$-sheets are indicated above the aligned sequences according to the crystal structure of $\alpha_1$-antitrypsin determined by Loebermann et al., supra, with minor corrections proposed by Bock et al., supra. The limited consensus sequence (Consensus) at the bottom of the alignment was derived as follows: the residue is listed if present in half or more sequences, a plus (+) is listed if conserved residues are present in two-thirds or more sequences. For this purpose, "conserved" means a positive score in the mutation data matrix [Dayhoff et al., supra]. Sequences are shown in single letter code. Residues removed from the mature proteins are shown in lower case. The arrowheads (→) indicate the active center.

The results of the above laboratory preparative work leading to the complete coding sequence of the cDNA clones representing the full size plasminogen activator inhibitor of the placental type (PAI-2) are further exemplified by the following detailed description of FIGS. 1 to 5 of the drawings.

Initially, 100,000 plaque-forming units from the placenta cDNA library were screened using the affinity purified antibody to human placental PAI. Two positive clones, λPAI-75.1 and λPAI-75.2, were found. Screening of the endothelial cell cDNA library yielded four positives among 80,000 recombinants: λPAI-T, λPAI-R, λPAI-89.2 and λPAI-89.3. The proteins induced by isopropyl-$\beta$-D-thiogalactopyranoside from these isolates were screened for PAI activity with a fibrin-agar spot assay (FIG. 1). A standard amount of human u-PA was spotted onto a gel containing fibrin and plasminogen. In the absence of any PAI, the added u-PA activates plasminogen to plasmin, which then degrades the fibrin to produce a cleared lytic zone. In the presence of PAI, lysis is prevented. Inhibition of fibrinolysis was observed only with the protein expressed by isolate λPAI-75.1. This inhibition was relieved by affinity-purified antibody to placenta PAI, but not by preimmune $\gamma$-globulin.

The protein expressed by each of these isolates was also tested for ability to form a covalent complex with u-PA (FIG. 2). Aliquots of λ-phage lysate were incubated with $^{125}$I-urokinase (two-chain), and any complexes formed were immunoprecipitated with affinity-purified anti-placental PAI. The immunoprecipitates were subjected to SDS-PAGE after reduction, and the mobility of the $^{125}$I-labeled complexes was determined by autoradiography. A complex of $M_r$ ~79,000 was formed with the protein expressed by λPAI-75.1 (FIG. 2, lane 5). The band at $M_r$~20,000 represents the light chain of two-chain urokinase. The heavy chain of urokinase has $M_r$ 33,000 suggesting that the protein expressed by λPAI-75.1 had contributed $M_r$~46,000 to the major complex detected. By Western blotting of λPAI-75.1 lysate proteins, the recombinant PAI was estimated to have $M_r$~45,000, slightly smaller than the natural placental PAI of $M_r$~47,000. This difference may reflect the lack of glycosylation of the protein expressed in *E. coli*. A faint band at $M_r$ ~88,000 was detected for isolate λPAI-89.3 (FIG. 2, lane 8). This may represent a distinct urokinase inhibitor which is recognized by the anti-placental PAI antibody. Preliminary sequence data for this cDNA insert shows that it is different from both the endothelial cell PAI and the placental PAI (FIG. 4). A minor band of similar mobility was also seen for λPAI-75.1 (FIG. 2, lane 5).

In the course of cDNA library screening, the strongest signals with the anti-PAI antibody were exhibited by isolates λPAI-75.1 and λPAI-T. The immunological relationship between the proteins expressed by these isolates and authentic placental PAI was tested by the method of "epitope selection", Weinberger et al., supra. Proteins induced by isopropyl-$\beta$-D-thiogalactopyranoside in *E. coli* infected by these λ-phage or by λgt11 were bound to nitrocellulose filters and used for affinity purification of the rabbit anti-human PAI antibody. Only isolate λPAI-75.1 yielded antibody that could recognize natural placental PAI (data not shown), suggesting that the protein expressed by this isolate and placental PAI share at least one epitope.

The cDNA insert of λPAI-75.1 did not cross-hybridize with any of the other positives identified with the antibody to placental PAI, and this insert was used to isolate additional clones by hybridization. Among 300,000 recombinants screened from the endothelial cell cDNA library, no positives were found. Among the same number of recombinants from the placental cDNA library, 15 positives were isolated.

Nucleotide Sequence of Placental PAI cDNA isolates

The cDNA insert of λPAI-75.1 was 1.9 kb in length and was sequenced by the strategy shown in FIG. 3. The entire sequence was determined on both strands and corresponds to nucleotides −52 to 1829 of FIG. 4, except that nucleotide −52 was G instead of A, and nucleotide 1829 was A instead of C. An oligonucleotide corresponding to the complement of residues −42 to −25 (FIG. 4) was used to screen 14 isolates obtained from the placental cDNA library with the cDNA insert of λPAI-75.1 as probe. One of these, λPAI-75.15, was also positive with the oligonucleotide probe. A single sequencing reaction from each end of this cDNA insert confirmed that λPAI-75.15 overlapped with λPAI-75.1, with three additional nucleotides at the 5'-end, and a poly(A) tail. Although isolated by hybridization, λPAI-75.15 was subsequently shown to express immunoreactive PAI of the same size as that of isolate λPAI-75.1 by Western blotting.

The combined sequence of λPAI-75.1 and λPAI-75.15 is shown in FIG. 4. The first ATG codon is preceded by a 5'-noncoding region of 55 nucleotides that contains a stop codon in-frame at residue −27. For isolate λPAI-75.1, this stop codon is also in-frame with the vector β-galactosidase coding sequence. The first ATG triplet is followed by an open reading frame of 1245 nucleotides, a stop codon, a 3'-noncoding region of 581 nucleotides, and a poly(A) tail. The sequence surrounding the initiator codon ACAATGG, differs only at position −1 from the proposed optimal sequence for initiation by eukaryotic ribosomes, ACCATGG [Kozak, *Cell* 44, 283–292 (1986)]. There are five potential polyadenylation or processing signals with the sequence AATAAA [Proudfoot and Brownlee, *Nature* 252, 359–362 (1981)]. Isolates λPAI-75.1 and λPAI-75.15 and a third partial cDNA clone (not shown) all share the same 3' terminus, 25–26 nucleotides after the pair of overlapping AATAAA sequences at residue 1804.

It will be understood that the "mature" human placental plasminogen activator inhibitor includes both PAI-2 and methionyl PAI-2 by virtue of the ATG translational codon in the expression vector construction herein.

EXAMPLE 2

Materials and Methods pKK223-3 is an expression vector for regulated overexpression of proteins from cloned genes in *E. coli*. It contains the strong trp-lac (tac) promoter first described by deBoer et al., *Proc. Natl. Acad. Sci. USA* 78, 21(1983).

JM 105 is an *E. coli* K12 lacI$^Q$ host described by Messing, *Nucleic Acids Res.* 9, 309–321 (1981), and *Gene* 15, 319–329 (1981). In the JM 105 host, the tac promoter is repressed but may be derepressed at the appropriate time by the addition of isopropyl β-thiogalactoside (IPTG).

pUC19 is a small *E. coli* plasmid cloning vehicle described by Yanich-Perron et al., *Gene* 33, 103–119 (1985). It consists of parts of pBR322 and M13mp19. pBR322 is the well-known workhorse plasmid of molecular biology described by Bolivar et al., *Gene* 2, 95 (1977) and Sutcliff, *Nucleic Acids Res.* 5, 2721–2728 (1978). M13mp19 is a wild type bacteriophage vector suitable for propagation on *E. coli* JM 105. When the pUC19 plasmid is introduced into JM 105, the plasmid gives rise to blue colonies on appropriate indicator plates. Cloning DNA fragments into any of the multiple restriction sites inactivates the lac gene, giving rise to white colonies.

BPV virus has a genome of 8.0 kilobases. It has the ability to be stably maintained in certain mouse cell lines, e.g. C-127. Foreign DNA, can be cloned into the BPV genome and thereby introduced into mouse cells. See *J. Virol.* 26, 291–298 (1978); *Virology* 103, 369–375 (1980); and Sarver et al., *Mol. Cell. Biol.* 1,486–496 (1981).

C-127 (ATCC CRL 1616) is a nontransformed clonal line derived from a mammary tumor of an RIII mouse.

All the foregoing are well-known, commercially available molecular biologicals.

A. Expression of placental PAI-2 in *E. coli*

PAI-2 was produced in *E. coli* strain JM 105 employing a trp-lac promoter vector, pKK 223-3 (obtained from Pharmacia) essentially as described by Amann et al., *Gene* 25, 167–178 (1983). A purified PAI 75.1/pUC19 plasmid was digested with EcoRI and the PAI 75.1 fragment was inserted into the EcoRI site of the pKK 223-3 vector. The chimeric plasmid was then used to transfect competent JM 105. The transfected cells were grown in the presence of ampicillin. Colonies were randomly picked, grown, and induced by isopropyl β-D-thiogalactoside (IPTG). The cells were lysed by sonication and the lysates were screened for the presence of PA inhibitory activity. As shown in FIG. 5, many clones (35% of randomly picked colonies) expressed relatively high level of PAI which inhibits the urokinase induced fibrin lysis in fibrin autography as evident by the non-clearing in 14 wells.

B. Expression of placental PAI-2 in mouse C-127 cells

PAI-2 was also be expressed in a mammalian cell, mouse C-127, employing a bovine papilloma virus (BPV) vector system as described by Howley et al., *Meth. Enzymol.* 101, 387–402 (1983). The PAI 75.1 DNA fragment was made blunt ended with the Klenow fragment of DNA polymerase I [Jacobson et al., *Eur. J. Biochem.* 45, 623–627 (1974)] by conventional procedure [Maniatis et al., eds., Molecular Cloning: A Laboratory Manual (1982)]. Then a Bam HI linker, d(CGGGATCCCG) was attached by incubation with T4 ligase and the resulting products were digested with BamHI. The Bam HI- PAI 75.1 was then inserted into the Bam HI site of the BPV vector, pMON 1123 (FIG. 6). Mouse C-127 cells were then transfected with the chimeric BPV vector essentially as described by Wigler et al., *Cell* 16, 777–785 (1979), and the transformants were selected for by G418 (genticin) resistance in accordance with methods described by Southern and Berg. *J. Molecular Applied Genetics* 1, 327–341 (1983). The transfected cells were then grown and the conditioned media were screened for urokinase inhibitory activities using fibrin autography assay similar to that shown in FIG. 5. Many clones (∼50% of randomly picked colonies) expressed relatively high levels of PAI which inhibits urokinase induced fibrin lysis.

Various other examples will be apparent to the person skilled in the art after reading the present disclosure without departing from the spirit and scope of the invention. All such further examples are included within the scope of the appended claims.

What is claimed is:

1. Human placental plasminogen activator inhibitor cDNA having the nucleotide sequence that follows:

```
−55 GTTAC CCGTCAGACA GCAACTCAGA
    GAATAACCAG AGAACAACCA GATTGAAACA      −1

ATG GAG GAT CTT TGT GTG GCA AAC ACA CTC
Met Glu Asp Leu Cys Val Ala Asn Thr Leu
                                       10

TTT GCC CTC AAT TTA TTC AAG CAT CTG GCA
Phe Ala Leu Asn Leu Phe Lys His Leu Ala
                                       20

AAA GCA AGC CCC ACC CAG AAC CTC TTC CTC       90
Lys Ala Ser Pro Thr Gln Asn Leu Phe Leu
                                       30

TCC CCA TGG AGC ATC TCG TCC ACC ATG GCC
Ser Pro Trp Ser Ile Ser Ser Thr Met Ala
                                       40

ATG GTC TAC ATG GGC TCC AGG GGC AGC ACC
Met Val Tyr Met Gly Ser Arg Gly Ser Thr
                                       50
```

-continued

| | | | | | | | | |
|---|---|---|---|---|---|---|---|---|
|GAA|GAC|CAG|ATG|GCC|AAG|GTG|CTT|CAG TTT| 180
|Glu|Asp|Gln|Met|Ala|Lys|Val|Leu|Gln Phe|
| | | | | | | | |60|

AAT GAA GTG GGA GCC AAT GCA GTT ACC CCC
Asn Glu Val Gly Ala Asn Ala Val Thr Pro
70

ATG ACT CCA GAG AAC TTT ACC AGC TGT GGG
Met Thr Pro Glu Asn Phe Thr Ser Cys Gly
80

TTC ATG CAG CAG ATC CAG AAG GGT AGT TAT    270
Phe Met Gln Gln Ile Gln Lys Gly Ser Tyr
90

CCT GAT GCG ATT TTG CAG GCA CAA GCT GCA
Pro Asp Ala Ile Leu Gln Ala Gln Ala Ala
100

GAT AAA ATC CAT TCA TCC TTC CGC TCT CTC
Asp Lys Ile His Ser Ser Phe Arg Ser Leu
110

AGC TCT GCA ATC AAT GCA TCC ACA GGG GAT    360
Ser Ser Ala Ile Asn Ala Ser Thr Gly Asp
120

TAT TTA CTG GAA AGT GTC AAT AAG CTG TTT
Tyr Leu Leu Glu Ser Val Asn Lys Leu Phe
130

GGT GAG AAG TCT GCG AGC TTC CGG GAA GAA
Gly Glu Lys Ser Ala Ser Phe Arg Glu Glu
140

TAT ATT CGA CTC TGT CAG AAA TAT TAC TCC    450
Tyr Ile Arg Leu Cys Gln Lys Tyr Tyr Ser
150

TCA GAA CCC CAG GCA GTA GAC TTC CTA GAA
Ser Glu Pro Gln Ala Val Asp Phe Leu Glu
160

TGT GCA GAA GAA GCT AGA AAA AAG ATT AAT
Cys Ala Glu Glu Ala Arg Lys Lys Ile Asn
170

TCC TGG GTC AAG ACT CAA ACC AAA GGC AAA    540
Ser Trp Val Lys Thr Gln Thr Lys Gly Lys
180

ATC CCA AAC TTG TTA CCT GAA GGT TCT GTA
Ile Pro Asn Leu Leu Pro Glu Gly Ser Val
190

GAT GGG GAT ACC AGG ATG GTC CTG GTG AAT
Asp Gly Asp Thr Arg Met Val Leu Val Asn
200

GCT GTC TAC TTC AAA GGA AAG TGG AAA ACT    630
Ala Val Tyr Phe Lys Gly Lys Trp Lys Thr
210

CCA TTT GAG AAG AAA CTA AAT GGG CTT TAT
Pro Phe Glu Lys Lys Leu Asn Gly Leu Tyr
220

CCT TTC CGT GTA AAC TCG GCT CAG CGC ACA
Pro Phe Arg Val Asn Ser Ala Gln Arg Thr
230

CCT GTA CAG ATG ATG TAC TTG CGT GAA AAG    720
Pro Val Gln Met Met Tyr Leu Arg Glu Lys
240

CTA AAC ATT GGA TAC ATA GAA GAC CTA AAG
Leu Asn Ile Gly Tyr Ile Glu Asp Leu Lys
250

GCT CAG ATT CTA GAA CTC CCA TAT GCT GGA
Ala Gln Ile Leu Glu Leu Pro Tyr Ala Gly
260

GAT GTT AGC ATG TTC TTG TTG CTT CCA GAT    810
Asp Val Ser Met Phe Leu Leu Leu Pro Asp
270

GAA ATT GCC GAT GTG TCC ACT GGC TTG GAG
Glu Ile Ala Asp Val Ser Thr Gly Leu Glu
280

CTG CTG GAA AGT GAA ATA ACC TAT GAC AAA
Leu Leu Glu Ser Glu Ile Thr Tyr Asp Lys
290

CTC AAC AAG TGG ACC AGC AAA GAC AAA ATG    900
Leu Asn Lys Trp Thr Ser Lys Asp Lys Met
300

GCT GAA GAT GAA GTT GAG GTA TAC ATA CCC
Ala Glu Asp Glu Val Glu Val Tyr Ile Pro
310

CAG TTC AAA TTA GAA GAG CAT TAT GAA CTC
Gln Phe Lys Leu Glu Glu His Tyr Glu Leu
320

AGA TCC ATT CTG AGA AGC ATG GGC ATG GAG    990
Arg Ser Ile Leu Arg Ser Met Gly Met Glu
330

GAC GCC TTC AAC AAG GGA CGG GCC AAT TTC
Asp Ala Phe Asn Lys Gly Arg Ala Asn Phe
340

TCA GGG ATG TCG GAG AGG AAT GAC CTG TTT
Ser Gly Met Ser Glu Arg Asn Asp Leu Phe
350

CTT TCT GAA GTG TTC CAC CAA GCC ATG GTG    1080
Leu Ser Glu Val Phe His Gln Ala Met Val
360

GAT GTG AAT GAG GAG GGC ACT GAA GCA GCC
Asp Val Asn Glu Glu Gly Thr Glu Ala Ala
370

GCT GGC ACA GGA GGT GTT ATG ACA GGG AGA
Ala Gly Thr Gly Gly Val Met Thr Gly Arg
380

ACT GGA CAT GGA GGC CCA CAG TTT GTG GCA    1170
Thr Gly His Gly Gly Pro Gln Phe Val Ala
390

GAT CAT CCG TTT CTT TTT CTT ATT ATG CAT
Asp His Pro Phe Leu Phe Leu Ile Met His
400

AAG ATA ACC AAG TGC ATT TTA TTT TTC GGC
Lys Ile Thr Lys Cys Ile Leu Phe Phe Gly
410

```
AGA TTT TGC TCA CCC TAA AAC TAA GCG TGC    1260
Arg Phe Cys Ser Pro End

TGCTTCTGCA AAAGATTTTT GTAGATGAGC

TGTGTGCCTC AGAATTGCTA TTTCAAATTG

CCAAAAATTT AGAGATGTTT TCTACATATT

TCTGCTCTTC TGAACAACTT                      1370

CTGCTACCCA CTAAATAAAA ACACAGAAAT

AATTAGACAA TTGTCTATTA TAACATGACA

ACCCTATTAA TCATTTGGTC TTCTAAAATG

GGATCATGCC CATTTAGATT                      1480

TTCCTTACTA TCAGTTTATT TTTATAACAT

TAACTTTTAC TTTGTTATTT ATTATTTTAT

ATAATGGTGA GTTTTTAAAT TATTGCTCAC
```

```
TGCCTATTTA ATGTAGCTAA                      1590

TAAAGTTATA GAAGCAGATG ATCTGTTAAT

TTCCTATCTA ATAAATGCCT TTAATTGTTC

TCATAATGAA GAATAAGTAG GTATCCCTCC

ATGCCCTTCT ATAATAAATA                      1700

TCTGGAAAAA ACATTAAACA ATAGGCAAAT

ATATGTTATG TGCATTTCTA GAAATACATA

ACACATATAT ATGTCTGTAT CTTATATTCA

ATTGCAAGTA TATAATAAAT                      1810

AAACCTGCTT CCAAACAACA AAAAAAAAAA

AAAAAAAAAA AAAAA.                          1855
```

2. Human placental plasminogen activator inhibitor cDNA having the nucleotide sequence that follows:

```
                                                            AC CCGTCAGACA GCAACTCAGA GAATAACCAG AGAACAACCA GATTGAAACA       -1

ATG GAG GAT CTT TGT GTG GCA AAC ACA CTC   TTT GCC CTC AAT TTA TTC AAG CAT CTG GCA   AAA GCA AGC CCC ACC CAG AAC CTC TTC CTC       90
Met Glu Asp Leu Cys Val Ala Asn Thr Leu   Phe Ala Leu Asn Leu Phe Lys His Leu Ala   Lys Ala Ser Pro Thr Gln Asn Leu Phe Leu
                  10                                        20                                        30

TCC CCA TGG AGC ATC TCG ACC ATG GCC   ATG GTC TAC ATG GGC TCC AGG GGC AGC ACC   GAA GCA CAG ATG GCC AAG GTG CTT CAG TTT       180
Ser Pro Trp Ser Ile Ser Thr Met Ala   Met Val Tyr Met Gly Ser Arg Gly Ser Thr   Glu Ala Gln Met Ala Lys Val Leu Gln Phe
              40                                       50                                        60

AAT GAA GTG GGA GCC AAT GCA GTT ACC CCC   ATG ACT CCA GAG AAC TTT ACC AGT TGT GGG   TTC ATG CAG CAG ATC CAG AAG GGT AGT TAT       270
Asn Glu Val Gly Ala Asn Ala Val Thr Pro   Met Thr Pro Glu Asn Phe Thr Ser Cys Gly   Phe Met Gln Gln Ile Gln Lys Gly Ser Tyr
                  70                                        80                                        90

CCT GAT GCG ATT TTG CAG GCA CAA GCT GCA   GAT AAA ATC CAT TCA CTT CGC TCT CTC   AGC TCT GCA ATC AAT GCA TCC ACA GGG GAT       360
Pro Asp Ala Ile Leu Gln Ala Gln Ala Ala   Asp Lys Ile His Ser Leu Arg Ser Leu   Ser Ser Ala Ile Asn Ala Ser Thr Gly Asp
                 100                                       110                                       120

TAT TTA CTG GAA AGT GTC AAT AAG CTG TTT   GGT GAG AAG TCT GCG AGC TTC CGG GAA GAA   TAT ATT CGA CTC TGT CAG AAA TAT TAC TCC       450
Tyr Leu Leu Glu Ser Val Asn Lys Leu Phe   Gly Glu Lys Ser Ala Ser Phe Arg Glu Glu   Tyr Ile Arg Leu Cys Gln Lys Tyr Tyr Ser
                 130                                       140                                       150

TCA CCC CAG GCA GTA GAC TTC CTA GAA   TGT GCA GAA GCT AGA AAA AAG ATT AAT   TCC TGG GTC AAG ACT CAA GGA TGG AAA ACT       540
Ser Pro Gln Ala Val Asp Phe Leu Glu   Cys Ala Glu Ala Arg Lys Lys Ile Asn   Ser Trp Val Lys Thr Gln Gly Trp Lys Thr
              160                                       170                                       180

ATC CCA AAC TTG TTA CCT GAA GGT TCT GTA   GAT GGG GAT ACC AGG ATG GTC CTG GTG AAT   GCT GTC TAC TTC AAA GGA TAT TTG TGT GAA AAG       630
Ile Pro Asn Leu Leu Pro Glu Gly Ser Val   Asp Gly Asp Thr Arg Met Val Leu Val Asn   Ala Val Tyr Phe Lys Gly Tyr Leu Cys Glu Lys
                 190                                       200                                       210

CCA TTT GAG AAG AAA CTA AAT GGG CTT TAT   CCT TTC CGT GTA AAC TCG GCT CAG CGC ACA   CCT GTA CAG ATG ATG TAC TTG CGT GAA AAG       720
Pro Phe Glu Lys Lys Leu Asn Gly Leu Tyr   Pro Phe Arg Val Asn Ser Ala Gln Arg Thr   Pro Val Gln Met Met Tyr Leu Arg Glu Lys
                 220                                       230                                       240

CTA AAC ATT GGA TAC ATA GAA GAC CTA AAG   GCT CAG ATT CTA GAA CTC CCA TAT GCT GGA   GAT GTT AGC ATG TTC TTG CTT CCA GAT       810
Leu Asn Ile Gly Tyr Ile Glu Asp Leu Lys   Ala Gln Ile Leu Glu Leu Pro Tyr Ala Gly   Asp Val Ser Met Phe Leu Leu Pro Asp
                 250                                       260                                       270

GAA ATT GCC GAT GTG TCC ACT GGC TTG GAG   CTG CTG GAA AGT GAA ATA ACC TAT GAC AAA   CTC AAC AAG TGG ACC AGC AAA ATG GCC AAA ATG       900
Glu Ile Ala Asp Val Ser Thr Gly Leu Glu   Leu Leu Glu Ser Glu Ile Thr Tyr Asp Lys   Leu Asn Lys Trp Thr Ser Lys Met Ala Lys Met
                 280                                       290                                       300

GCT GAA GAT GAA GTT GAG GTA GAA GTT GAG   CAG TTC AAA TTA GAA GAG CAT TAT GAA CTC   AGA TCC ATT CTG AGA AGC ATG GGC ATG GAG       990
Ala Glu Asp Glu Val Glu Val Tyr Glu Val   Gln Phe Lys Leu Glu Glu His Tyr Glu Leu   Arg Ser Ile Leu Arg Ser Met Gly Met Glu
                 310                                       320                                       330

GAC GCC TTC AAC GAG GAG GGA ACT GAA GCA CGG   GCC CGG GCC CGG AAT GAC TTC TTC   CTT TCT GAA GTG GTG TTC CAC CAA GCC ATG GTG       1080
Asp Ala Phe Asn Glu Glu Gly Thr Glu Ala Arg   Ala Arg Ala Arg Asn Asp Leu Phe   Leu Ser Glu Val Val Phe His Gln Ala Met Val
                 340                                       350                                       360

GAT GTG AAT GAG GAG GGC ACT GGA GGT GTT ATG ACA GGG AGA   GCT GGC ACA GGA GGT GTT ATG ACA GGG AGA   ACT GGA CAT GGA GGC CCA CAG TTT GTG GCA       1170
Asp Val Asn Glu Glu Gly Thr Gly Gly Val Met Thr Gly Arg    Ala Gly Thr Gly Gly Val Met Thr Gly Arg    Thr Gly His Gly Gly Pro Gln Phe Val Ala
                 370                                        380                                        390
```

-continued

| | | | |
|---|---|---|---|
| GAT CAT CCG TTT CTT TTT CTT ATT ATG CAT<br>Asp His Pro Phe Leu Phe Leu Ile Met His<br>400 | AAG ATA ACC AAG TGC ATT TTA TTT TTC GGC<br>Lys Ile Thr Lys Cys Ile Leu Phe Phe Gly<br>410 | AGA TTT TGC TCA CCC TAA AAC TAA GCG TGC<br>Arg Phe Cys Ser Pro End | 1260 |

TGCTTCTGCA AAAGATTTTT GTAGATGAGC TGTGTGCCTC AGAATTGCTA TTTCAAATTG CCAAAAATTT AGAGATGTTT TCTACATATT TCTGCTCTTC TGAACAACTT   1370

CTGCTACCCA CTAAATAAAA ACACAGAAAT AATTAGACAA TTGTCTATTA TAACATGACA ACCCTATTAA TCATTGGTC TTCTAAAATG GGATCATGCC CATTTAGATT   1480

TTCCTTACTA TCAGTTTATT TTTATAACAT TAACTTTTAC TTTGTTTATT ATTATTTTAT ATAATGGTGA GTTTTTAAAT TATTGCTCAC TGCCTATTA ATGTAGCTAA   1590

TAAAGTTATA GAAGCAGATG ATCTGTTAAT TTCCTATCTA ATAAATGCCT TTAATTGTTC TCATAATGAA GAATAAGTAG GTATCCCTCC ATGCCCTTCT ATAATAAATA   1700

TCTGGAAAAA ACATTAAACA ATAGGCAAAT ATATGTTATG TGCATTTCTA GAAATACATA ACACATATAT ATGTCTGTAT CTTATATTCA ATTGCAAGTA TATAATAAAT   1810

AAACCTGCTT CCAAACAAC.

3. A recombinant DNA sequence comprising a sequence encoding human placental plasminogen activator inhibitor, said human placental plasminogen activator inhibitor having the amino acid sequence that follows:

Met Glu Asp Leu Cys Val Ala Asn Thr Leu Phe Ala Leu Asn Leu Phe Lys His Leu Ala Lys Ala Ser Pro Thr Gln Asn Leu Phe Leu
                10                              20                              30

Ser Pro Trp Ser Ile Ser Ser Thr Met Ala Met Val Tyr Met Gly Ser Arg Gly Ser Thr Glu Asp Gln Met Ala Lys Val Leu Gln Phe
                40                              50                              60

Asn Glu Val Gly Ala Asn Ala Val Thr Pro Met Thr Pro Glu Asn Phe Thr Ser Cys Gly Phe Met Gln Gln Ile Gln Lys Gly Ser Tyr
                70                              80                              90

Pro Asp Ala Ile Leu Gln Ala Gln Ala Ala Asp Lys Ile His Ser Ser Phe Arg Ser Leu Ser Ser Ala Ile Asn Ala Ser Thr Gly Asp
                100                             110                             120

Tyr Leu Leu Glu Ser Val Asn Lys Leu Phe Gly Glu Lys Ser Ala Ser Phe Arg Glu Glu Tyr Ile Arg Leu Cys Gln Lys Tyr Tyr Ser
                130                             140                             150

Ser Glu Pro Gln Ala Val Asp Phe Leu Glu Cys Ala Glu Glu Ala Arg Lys Lys Ile Asn Ser Trp Val Lys Thr Gln Thr Lys Gly Lys
                160                             170                             180

Ile Pro Asn Leu Leu Pro Glu Gly Ser Val Asp Gly Asp Thr Arg Met Val Leu Val Asn Ala Val Tyr Phe Lys Gly Lys Trp Lys Thr
                190                             200                             210

Pro Phe Glu Lys Lys Leu Asn Gly Leu Tyr Pro Phe Arg Val Asn Ser Ala Gln Arg Thr Pro Val Gln Met Met Tyr Leu Arg Glu Lys
                220                             230                             240

Leu Asn Ile Gly Tyr Ile Glu Asp Leu Lys Ala Gln Ile Leu Glu Leu Pro Tyr Ala Gly Asp Val Ser Met Phe Leu Leu Leu Pro Asp
                250                             260                             270

Glu Ile Ala Asp Val Ser Thr Gly Leu Glu Leu Leu Glu Ser Glu Ile Thr Tyr Asp Lys Leu Asn Lys Trp Thr Ser Lys Asp Lys Met
                280                             290                             300

Ala Glu Asp Glu Val Glu Val Tyr Ile Pro Gln Phe Lys Leu Glu Glu His Tyr Glu Leu Arg Ser Ile Leu Arg Ser Met Gly Met Glu
                310                             320                             330

Asp Ala Phe Asn Lys Gly Arg Ala Asn Phe Ser Gly Met Ser Glu Arg Asn Asp Leu Phe Leu Ser Glu Val Phe His Gln Ala Met Val
                340                             350                             360

Asp Val Asn Glu Glu Gly Thr Glu Ala Ala Ala Gly Thr Gly Gly Val Met Thr Gly Arg Thr Gly His Gly Gly Pro Gln Phe Val Ala
                370                             380                             390

Asp His Pro Phe Leu Phe Leu Ile Met His Lys Ile Thr Lys Cys Ile Leu Phe Phe Gly Arg Phe Cys Ser Pro.
                400                             410

4. A replicable expression vector comprising the DNA sequence of claim 3.

5. A viable cell culture transfected with the expression vector of claim 4.

6. A bacterial cell culture transformed with the expression vector of claim 4 capable of producing mature human placental plasminogen activator inhibitor.

7. A mammalian cell culture transformed with the expression vector of claim 4 capable of producing mature human placental plasminogen activator inhibitor.

8. A process which comprises expressing a gene encoding human placental plasminogen activator inhibitor having the amino acid sequence that follows:

| Met | Glu | Asp | Leu | Cys | Val | Ala | Asn | Thr | Leu |
|-----|-----|-----|-----|-----|-----|-----|-----|-----|-----|
|     |     |     |     |     |     |     |     |     | 10  |
| Phe | Ala | Leu | Asn | Leu | Phe | Lys | His | Leu | Ala |
|     |     |     |     |     |     |     |     |     | 20  |
| Lys | Ala | Ser | Pro | Thr | Gln | Asn | Leu | Phe | Leu |
|     |     |     |     |     |     |     |     |     | 30  |
| Ser | Pro | Trp | Ser | Ile | Ser | Ser | Thr | Met | Ala |
|     |     |     |     |     |     |     |     |     | 40  |
| Met | Val | Tyr | Met | Gly | Ser | Arg | Gly | Ser | Thr |
|     |     |     |     |     |     |     |     |     | 50  |
| Glu | Asp | Gln | Met | Ala | Lys | Val | Leu | Gln | Phe |
|     |     |     |     |     |     |     |     |     | 60  |
| Asn | Glu | Val | Gly | Ala | Asn | Ala | Val | Thr | Pro |
|     |     |     |     |     |     |     |     |     | 70  |
| Met | Thr | Pro | Glu | Asn | Phe | Thr | Ser | Cys | Gly |
|     |     |     |     |     |     |     |     |     | 80  |
| Phe | Met | Gln | Gln | Ile | Gln | Lys | Gly | Ser | Tyr |
|     |     |     |     |     |     |     |     |     | 90  |
| Pro | Asp | Ala | Ile | Leu | Gln | Ala | Gln | Ala | Ala |
|     |     |     |     |     |     |     |     |     | 100 |
| Asp | Lys | Ile | His | Ser | Ser | Phe | Arg | Ser | Leu |
|     |     |     |     |     |     |     |     |     | 110 |
| Ser | Ser | Ala | Ile | Asn | Ala | Ser | Thr | Gly | Asp |
|     |     |     |     |     |     |     |     |     | 120 |
| Tyr | Leu | Leu | Glu | Ser | Val | Asn | Lys | Leu | Phe |
|     |     |     |     |     |     |     |     |     | 130 |
| Gly | Glu | Lys | Ser | Ala | Ser | Phe | Arg | Glu | Glu |
|     |     |     |     |     |     |     |     |     | 140 |
| Tyr | Ile | Arg | Leu | Cys | Gln | Lys | Tyr | Tyr | Ser |
|     |     |     |     |     |     |     |     |     | 150 |
| Ser | Glu | Pro | Gln | Ala | Val | Asp | Phe | Leu | Glu |
|     |     |     |     |     |     |     |     |     | 160 |
| Cys | Ala | Glu | Glu | Ala | Arg | Lys | Lys | Ile | Asn |
|     |     |     |     |     |     |     |     |     | 170 |
| Ser | Trp | Val | Lys | Thr | Gln | Thr | Lys | Gly | Lys |
|     |     |     |     |     |     |     |     |     | 180 |

| | | | | | | | | |
|---|---|---|---|---|---|---|---|---|
| Ile | Pro | Asn | Leu | Leu | Pro | Glu | Gly | Ser | Val 190 |
| Asp | Gly | Asp | Thr | Arg | Met | Val | Leu | Val | Asn 200 |
| Ala | Val | Tyr | Phe | Lys | Gly | Lys | Trp | Lys | Thr 210 |
| Pro | Phe | Glu | Lys | Lys | Leu | Asn | Gly | Leu | Tyr 220 |
| Pro | Phe | Arg | Val | Asn | Ser | Ala | Gln | Arg | Thr 230 |
| Pro | Val | Gln | Met | Met | Tyr | Leu | Arg | Glu | Lys 240 |
| Leu | Asn | Ile | Gly | Tyr | Ile | Glu | Asp | Leu | Lys 250 |
| Ala | Gln | Ile | Leu | Glu | Leu | Pro | Tyr | Ala | Gly 260 |
| Asp | Val | Ser | Met | Phe | Leu | Leu | Leu | Pro | Arg 270 |
| Glu | Ile | Ala | Asp | Val | Ser | Thr | Gly | Leu | Glu 280 |
| Leu | Leu | Glu | Ser | Glu | Ile | Thr | Tyr | Asp | Lys 290 |
| Leu | Asn | Lys | Trp | Thr | Ser | Lys | Asp | Lys | Met 300 |
| Ala | Glu | Asp | Glu | Val | Glu | Val | Tyr | Ile | Pro |
| Gln | Phe | Lys | Leu | Glu | Glu | His | Tyr | Glu | Leu 320 |
| Arg | Ser | Ile | Leu | Arg | Ser | Met | Gly | Met | Glu 330 |
| Asp | Ala | Phe | Asn | Lys | Gly | Arg | Ala | Asn | Phe 340 |
| Ser | Gly | Met | Ser | Glu | Arg | Asn | Asp | Leu | Phe 350 |
| Leu | Ser | Glu | Val | Phe | His | Gln | Ala | Met | Val 360 |
| Asp | Val | Asn | Glu | Glu | Gly | Thr | Glu | Ala | Ala 370 |
| Ala | Gly | Thr | Gly | Gly | Val | Met | Thr | Gly | Arg 380 |
| Thr | Gly | His | Gly | Gly | Pro | Gln | Phe | Val | Ala 390 |
| Asp | His | Pro | Phe | Leu | Phe | Leu | Ile | Met | His 400 |
| Lys | Ile | Thr | Lys | Cys | Ile | Leu | Phe | Phe | Gly 410 |
| Arg | Phe | Cys | Ser | Pro | | | | | | in a bacterial or mammalian cell culture transformed with a DNA expression vector containing said gene operably linked to transcription and translation sequences in said vector and recovering said human placental plasminogen activator inhibitor.

* * * * *